United States Patent
Bourelle et al.

(10) Patent No.: US 11,744,777 B2
(45) Date of Patent: Sep. 5, 2023

(54) RECONSTITUTION DEVICE, SYSTEM AND METHOD

(71) Applicant: Enable Injections, Inc., Cincinnati, OH (US)

(72) Inventors: Dylan Bourelle, Cincinnati, OH (US); Matthew Huddleston, Loveland, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 842 days.

(21) Appl. No.: 16/492,849

(22) PCT Filed: Mar. 9, 2018

(86) PCT No.: PCT/US2018/021811
§ 371 (c)(1),
(2) Date: Sep. 10, 2019

(87) PCT Pub. No.: WO2018/165588
PCT Pub. Date: Sep. 13, 2018

(65) Prior Publication Data
US 2020/0146938 A1 May 14, 2020

Related U.S. Application Data

(60) Provisional application No. 62/520,335, filed on Jun. 15, 2017, provisional application No. 62/469,870, filed on Mar. 10, 2017.

(51) Int. Cl.
*A61J 1/20* (2006.01)
*A61J 1/14* (2023.01)
(Continued)

(52) U.S. Cl.
CPC ............ *A61J 1/2062* (2015.05); *A61J 1/1406* (2013.01); *A61J 1/16* (2013.01); *A61J 1/18* (2013.01);
(Continued)

(58) Field of Classification Search
CPC ...... A61J 1/2075; A61J 1/2082; A61J 1/2096; A61J 1/2013; A61J 1/2062; A61J 1/1406;
(Continued)

(56) References Cited

U.S. PATENT DOCUMENTS 5,466,220 A * 11/1995 Brenneman ........... A61J 1/2096
604/87
6,364,865 B1 * 4/2002 Lavi ....................... A61M 5/19
604/411

(Continued)

FOREIGN PATENT DOCUMENTS

JP    2003-80169 A    3/2003
JP    2014-503280 A   2/2014
(Continued)

OTHER PUBLICATIONS

Extended European Search Report issued from the European Patent Office for EP Application No. EP18763995.0, dated Oct. 19, 2020 (9 pages).

(Continued)

*Primary Examiner* — Nicolas A Arnett
(74) *Attorney, Agent, or Firm* — Cook Alex Ltd.

(57) ABSTRACT

A disposable fluid transfer and mixing device is disclosed and includes an injector support surface for receiving an injection device thereon. A lyophilized drug vial, a diluent vial and a syringe are also attached to the device. The device features fluid passageways and a manual valve that may be manipulated so that the syringe may be used to transfer diluent from the diluent vial to the lyophilized drug vial, for (Continued)

reconstitution of the drug. The valve may also be configured so that the reconstituted drug is transferred from the lyophilized drug vial to the injection device. An automated transfer and mixing device receives an injection device, a lyophilized drug vial and a diluent vial and transfers diluent from the diluent vial to the lyophilized drug vial and shakes or vibrates the lyophilized drug vial to reconstitute the drug. The device then transfers the reconstituted drug from the lyophilized drug vial to the injection device.

4 Claims, 21 Drawing Sheets

(51) Int. Cl.
*A61J 1/16* (2023.01)
*A61J 1/18* (2023.01)
*B01F 31/20* (2022.01)
*A61M 5/20* (2006.01)
*B01F 101/00* (2022.01)

(52) U.S. Cl.
CPC ............... *A61J 1/20* (2013.01); *A61J 1/201* (2015.05); *A61J 1/2037* (2015.05); *A61J 1/2048* (2015.05); *A61J 1/2075* (2015.05); *A61J 1/2082* (2015.05); *A61J 1/2096* (2013.01); *A61M 5/2066* (2013.01); *B01F 31/265* (2022.01); *A61J 2200/76* (2013.01); *A61J 2205/20* (2013.01); *B01F 2101/2202* (2022.01); *B01F 2215/0454* (2013.01)

(58) Field of Classification Search
CPC ........ A61J 1/16; A61J 1/18; A61J 1/20; A61J 1/201; A61J 1/2037; A61J 1/2048; A61J 2200/76; A61J 2205/20; A61M 5/2066; A61M 5/19; A61M 5/3287; A61M 5/46; A61M 5/14248; A61M 5/165; A61M 5/168; A61M 5/172; A61M 5/142; A61M 2205/18; A61M 2205/584; A61M 2205/75; A61M 2205/7536; B01F 31/265; B01F 2101/2202; B01F 2215/0454
See application file for complete search history.

(56) References Cited

U.S. PATENT DOCUMENTS

| | | | | |
|---|---|---|---|---|
| 6,641,565 | B1 * | 11/2003 | Lavi | A61M 5/148 |
| | | | | 141/346 |
| 7,896,849 | B2 * | 3/2011 | Delay | A61J 1/2089 |
| | | | | 604/82 |
| 9,662,621 | B2 * | 5/2017 | Beyer | B01F 35/32005 |
| 9,895,487 | B2 * | 2/2018 | Duncan | A61M 5/19 |
| 9,925,333 | B2 * | 3/2018 | Hooven | A61M 5/20 |
| 10,363,367 | B2 * | 7/2019 | Mueller-Pathle | A61M 5/2033 |
| 10,507,285 | B2 * | 12/2019 | Dunki-Jacobs | A61M 5/152 |
| 10,675,628 | B2 * | 6/2020 | Olivier | G01N 1/38 |
| 11,419,790 | B2 * | 8/2022 | Yodfat | A61J 1/22 |
| 2004/0069044 | A1 * | 4/2004 | Lavi | A61M 5/19 |
| | | | | 604/93.01 |
| 2013/0274656 | A1 * | 10/2013 | Dehan | A61M 5/20 |
| | | | | 604/82 |
| 2013/0292002 | A1 * | 11/2013 | Lopez | A61J 1/2096 |
| | | | | 141/83 |
| 2013/0296807 | A1 * | 11/2013 | Lintern | A61M 5/158 |
| | | | | 604/404 |
| 2014/0290796 | A1 * | 10/2014 | Tribble | B65B 7/2821 |
| | | | | 141/94 |
| 2015/0029816 | A1 * | 1/2015 | Beyer | A61J 1/20 |
| | | | | 366/167.1 |
| 2016/0106921 | A1 * | 4/2016 | Fraunhofer | A61M 5/2066 |
| | | | | 604/89 |
| 2017/0246085 | A1 * | 8/2017 | Kriheli | A61M 5/1782 |
| 2021/0145697 | A1 * | 5/2021 | Bourelle | A61M 5/14248 |

FOREIGN PATENT DOCUMENTS

| | | |
|---|---|---|
| JP | 2015-509421 A | 3/2015 |
| JP | 2016-524513 A | 8/2016 |
| WO | 2014029433 A1 | 2/2014 |
| WO | 2014204894 A2 | 12/2014 |

OTHER PUBLICATIONS

International Search Report and Written Opinion of the ISA for PCT Application No. PCT/US2018/021811, dated Jul. 9, 2018 (14 pages).
Notification of Reasons for Refusal, counterpart Japanese App No. 2021-145575, with English translation (dated Jun. 7, 2022) (6 pages).

* cited by examiner

RECONSTITUTION DEVICE, SYSTEM AND METHOD

The present application is the U.S. National Stage of a PCT International Patent Application No. PCT/US2018/021811, filed Mar. 9, 2018, which claims priority to and the benefit of U.S. Provisional Patent Application Ser. No. 62/469,870, filed Mar. 10, 2017, and U.S. Provisional Patent Application Ser. No. 62/520,335, filed Jun. 15, 2017 the contents of both which are hereby incorporated herein by reference.

FIELD OF THE INVENTION

The present subject matter relates generally to transfer devices for mixing, diluting or reconstituting a medication and transferring the resulting liquid medication into an injection device.

BACKGROUND

Injection devices that are worn by a patient temporarily or for extended period are well known in the medical field. The subject matter of this application relates to a transfer device for use particularly but not exclusively with the injection device described in PCT Published Application No. WO 2014/204894, published Dec. 24, 2014, and which is hereby incorporated by reference in its entirety. That injection device includes an internal resilient bladder that may be filled with any suitable injectable medicament, whether drug, antibiotic, biologic or other injectable, for subcutaneous injection, typically a bolus injection, into a patient while the device is being worn by the patient.

This injection device must be filled (wholly or partially) with the desired injectable before injection into the patient. In some situations, the injectable must be diluted or reconstituted.

There has been an increase in the use of such injection devices due to an increase in the number of therapeutic biologics administered subcutaneously (SC) rather than intravenously (IV). The injections allow for more flexibility for patients/caregivers and increase the overall quality of life of the patients/caregivers.

The formulations of injectables, however, are typically unstable over long periods of time at room temperatures. For example, high protein concentrations require refrigeration to increase shelf-life. As a result, the option of freeze drying or lyophilizing the formulations have become attractive. Such an approach, however, requires manual reconstitution of the product prior to administration.

The process for reconstitution of a lyophilized drug includes a number of steps required by the user. For example, the process is typically carried out using two separate vials (one filled with diluent, the other with the lyophilized medication). The user must use syringe to retract diluent from the first vial and transfer it to the second/lyophilized vial. Then the user must manually shake/roll the second vial for an extended period of time after which he or she must visually inspect the vial and determine if the medication is sufficiently reconstituted. The overall complexity and time consumption of the process leads to issues regarding compliance, safety, and ease of administration for the patients/caregivers.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a disposable fluid transfer device includes an injector support surface configured to receive an injection device thereon. A fluid transfer port extends upwardly from the support surface for transfer of liquid into an injection device when received on the support surface. A lyophilized drug vial adapter is configured to receive a vial containing a lyophilized drug, while a diluent vial adapter is configured to receive a vial containing a diluent. A syringe adapter is configured to receive a syringe. A fluid flow path may be placed in communication between the lyophilized drug vial adapter and syringe adapter, between the diluent vial adapter and the syringe adapter and between the syringe adapter and the fluid transfer port. A manual valve in the fluid flow path selectively places the diluent vial adapter in communication with the syringe adapter, the lyophilized drug vial adapter in communication with the syringe adapter or the syringe adapter in communication with fluid transfer port.

In another aspect, a device for reconstituting a lyophilized product features a housing including a vial receptacle. A vial holder is configured to be connected to the vial receptacle of the housing and to hold a first vial containing a lyophilized product and a second vial containing a diluent. A pressurized fluid supply system is configured to transfer diluent from the second vial to the first vial. A motor is configured to be connected to the vial holder when the vial holder is connected to the vial receptacle. The motor vibrates the first vial so that the lyophilized product in the first vial is reconstituted with diluent transferred from the second vial to the first vial.

In another aspect, a system for injecting a drug includes an injection device and a device for reconstituting a lyophilized drug. The device for reconstituting the lyophilized drug includes a vial holder configured to hold a first vial containing a lyophilized drug and a second vial containing a diluent. A pressurized fluid supply system is configured to transfer diluent from the second vial to the first vial and to transfer a reconstituted drug from the first vial to the injection device. A motor is connected to the vial holder and is configured to vibrate the first vial so that the lyophilized drug in the first vial is reconstituted with diluent transferred from the second vial to the first vial.

In still another aspect, a method for reconstituting a drug includes the steps of providing a first vial containing a lyophilized drug and a second vial containing a diluent, transferring diluent from the second vial to the first vial and vibrating the first vial so that the lyophilized drug in the first vial is reconstituted with the diluent from the second vial.

In still another aspect, a device for reconstituting a lyophilized product includes a vial receptacle configured to hold a first vial containing a lyophilized product and a second vial containing a diluent. A pressurized fluid supply system is configured to transfer diluent from the second vial to the first vial. A motor is configured to vibrate the first vial when the first vial is held by the vial receptacle so that the lyophilized product in the first vial is reconstituted with diluent transferred from the second vial to the first vial.

DETAILED DESCRIPTION

Injection Device

FIGS. 1-20 of this application and the related description extending from this paragraph to the section entitled "Transfer Device" are largely taken from commonly owned prior published PCT Application No. WO 2014/204894 A2, International Filing Date Jun. 17, 2014, which is hereby incorporated by reference herein in its entirety.

Figure 1:
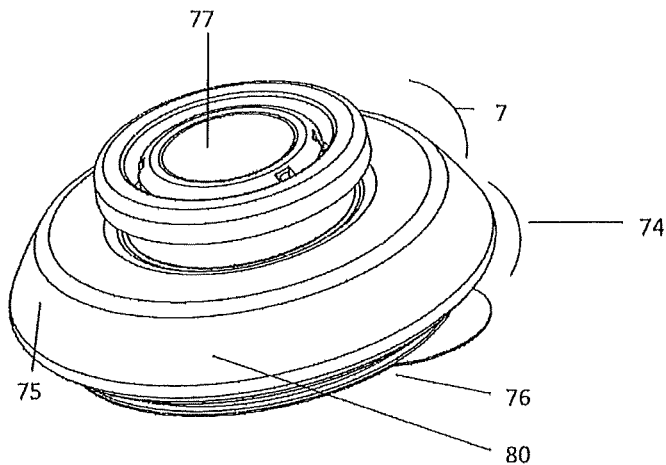
FIG. 1 is a perspective view of the injection device.
Figure 2:
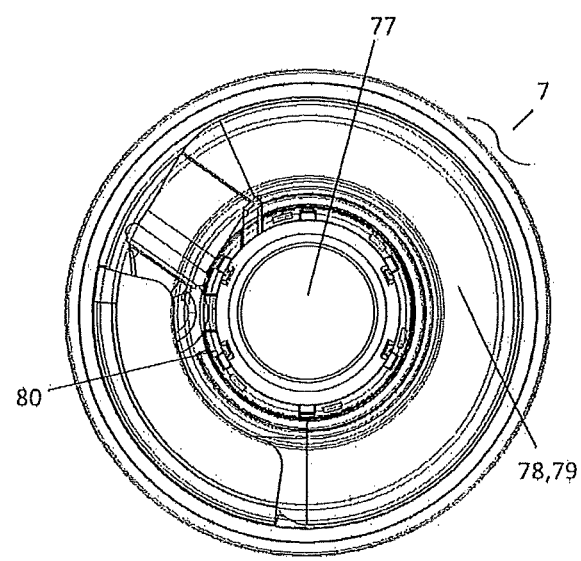
FIG. 2 is a top view of a filled injection device showing the delivery indicator in a full state.
Figure 3:
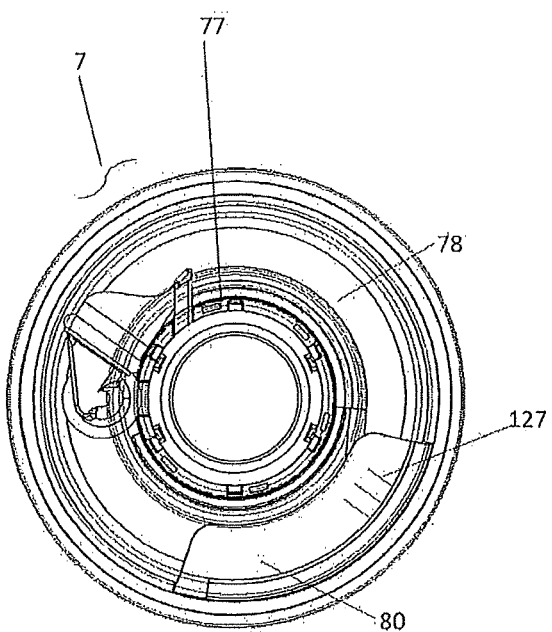
FIG. 3 is top view of a filled injection device showing the delivery indicator in an empty state.

Referring to FIGS. 1-3, the injection device 7 may be of any suitable configuration, but as illustrated it has a generally low-profile, disc shaped outer housing 74 with an upper surface 75 and a lower surface 76, through which an injection needle or cannula protrudes when actuated by the user. The upper surface 75 has an actuator or button 77 to start the injection and a clear section 80 of the housing 74 that allows the subject or medical professional to view the expandable member 78 to ascertain the amount of injectable fluid 79 in the device 7. For example, the user could determine whether the injection has commenced or concluded. More preferably, the expandable member 78 and/or the clear section 80 of the housing 74 may be graduated, such as by line markings 127 or the like, so that the patient or medical professional can visually determine the amount of injectable fluid 79 remaining with greater precision—such as, for example, about 50% complete or about 75% complete. In addition, the expandable member 78 may itself include or interact with a feature on the outer housing 74 to show the amount of injectable fluid 79 remaining.

It should be noted that "injectable fluid," "injectable," "drug," "medicament" and like terms are used interchangeably herein. For example, when the injection device 7 is full of drug 79, the clear section 80 may show one color such as but not limited to green. When the injection device 7 is empty of drug 79, the clear section 80 may show a different color such as but not limited to red. In the middle of dispense, the clear section 80 could show a combination of colors.

Figure 4:
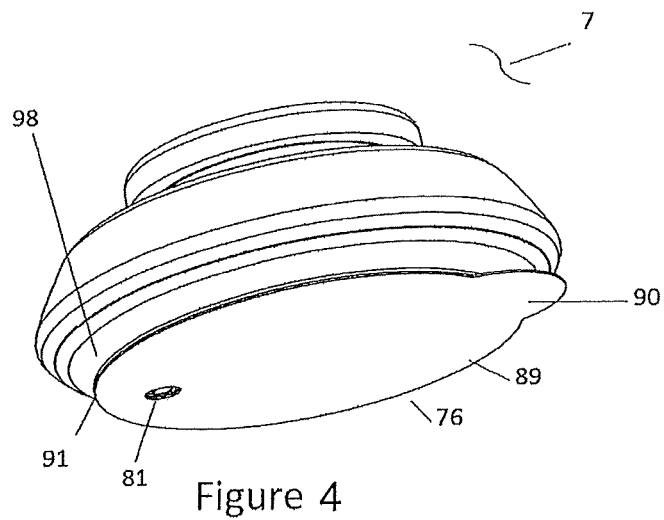
FIG. 4 is a perspective view showing the underside of the injection device with attached tape and fill port.
Figure 5:
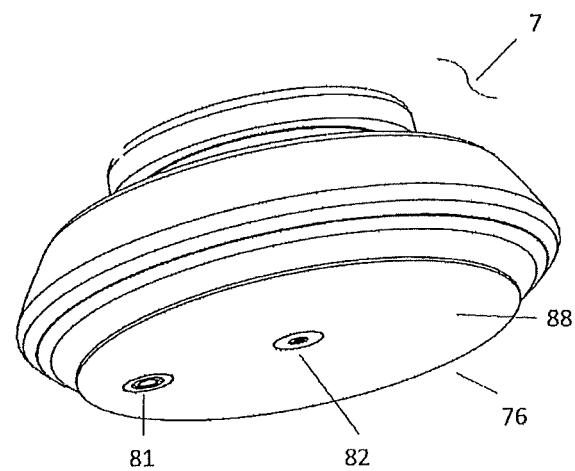
FIG. 5 is a perspective view showing the underside of the injection device with tape detached and the fill and dispense ports exposed.
Figure 6:
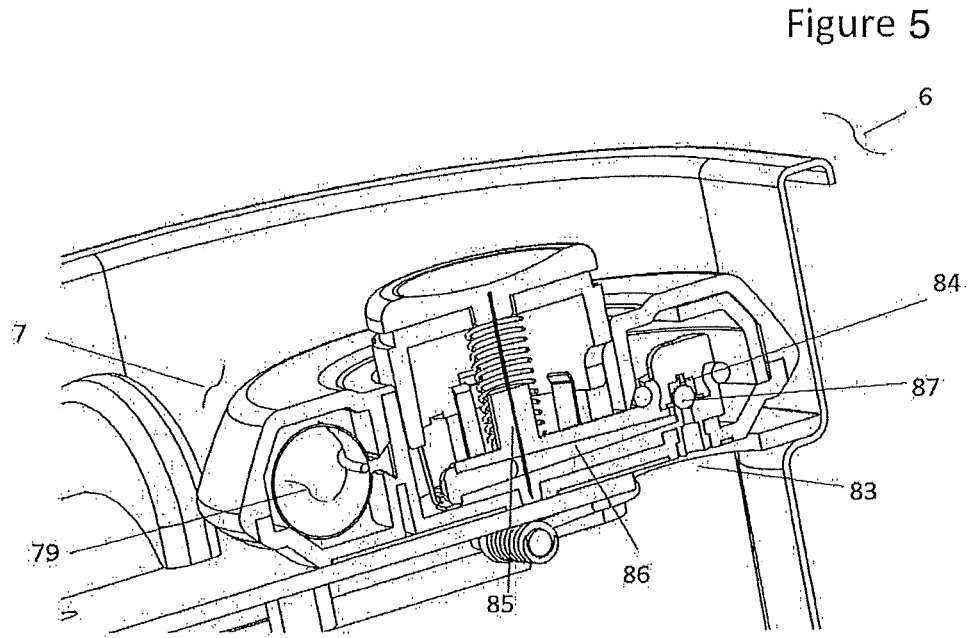
FIG. 6 is a cross-section of the injection device on the transfer apparatus.

Referring to FIGS. 4-6, the undersurface 76 of the injection device 7 includes a filling port 81 and a dispense port 82. The filling port 81 is the interface that allows the transfer apparatus filling tube 83 to transfer liquid 79 to the injection device 7. The dispense port 82 also contains an internal pathway 84 between the expelled injectable 79 from the expandable member 78 and the needle 85. The filling port 81 and dispense port 79 may be in direct fluid communication through internal pathways 86, or they may be combined into a single port.

Referring to FIGS. 4-6, the injection device may preferably include a filling port 81 that includes a check valve 87 to prevent pressurized injectable 79 from leaking out of the injection device 7 when the injection device 7 is removed from the transfer apparatus 6 and the filling port 81 is removed from the filling tube 83.

Referring to FIGS. 4-6, the injection device 7 may also have a filling port 81 that is configured to accept the insertion of a syringe. This syringe may be configured with a luer fitting or a needle. This filling port 81 configuration allows for the manual filling of the injection device by the user. The transfer apparatus 6 may still be used but would not be required in this configuration.

Referring to FIGS. 4-6, the injection device 7 may also have a dispense port 82 that is configured to directly connect to an intravenous cannula via attached tubing or a standard needle port.

Referring to FIGS. 4-6, the undersurface 76 of the injection device 7 carries an adhesive 88 for securing the injection device 7 temporarily to the skin of a subject until the injection is complete. During removal of the injection device 7, an adhesive tape liner 89 may be removed automatically exposing an adhesive surface 88 on the undersurface 76 of the injection device 7 that may be used to adhere the injection device 7 to the patient's skin. Alternatively, the tape liner 89 may have a tab 90 that the user pulls to manually remove before adhering the injection device 7 to the skin. Alternatively this tab may be attached to the surface of the transfer device 4 so that the tape liner is automatically removed upon removal of the injection device 7.

Referring to FIGS. 4-6, the injection device 7 may have an adhesive tape flange 91 that extends beyond the undersurface base 76. This flange 91 of adhesive tape 88 can act as a strain relief between the injection device 7 and skin surface, reducing the risk of accidentally dislodging the injection device 7 from the skin. In other words, similar to a tapered strain relief on a wire where it enters into a connector, the extended adhesive flange 91 acts to distribute the load on both sides of the connection point between the adhesive tape 88 and the undersurface base 76 of the injection device 7 to reduce any stress risers at the adhesive tape 88 and skin interface.

Referring to FIGS. 4-6, the injection device 7 may be configured with a tapered underside surface 98 that presses on the adhesive flange 91 to securely attach the adhesive tape 88 to the skin as the user is securing the injection device 7 to the skin without additional user intervention. By using the compliance of a person's skin when pressing the injection device 7 against the skin, the tapered underside surface 98 of the injection device 7 effectively presses the flange 91 of the adhesive tape 88 against the skin but the upper exposed surface of the flange 91 portion does not have exposed adhesive and therefore is not attached to that portion of the tapered underside surface 98. The user is not required to run their finger around the flange 91 to secure the injection device 7 to the skin making it a much simpler method of adhesive tape 88 attachment.

Referring to FIGS. 4-6, the injection device 7 may have an underside surface 76 that is flexible or compliant in lieu of being rigid to allow for improved attachment by conforming of the injection device 7 to the skin during application.

Figure 7:
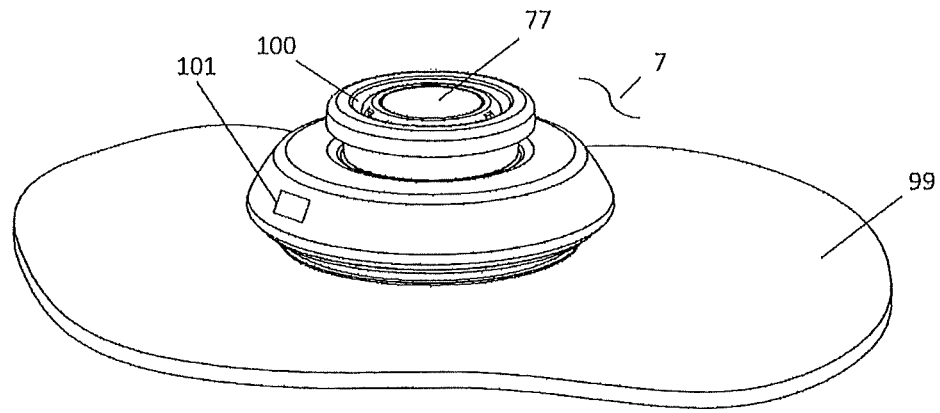
FIG. 7 is a perspective view of the injection device attached to the skin with the safety device installed.
Figure 8:
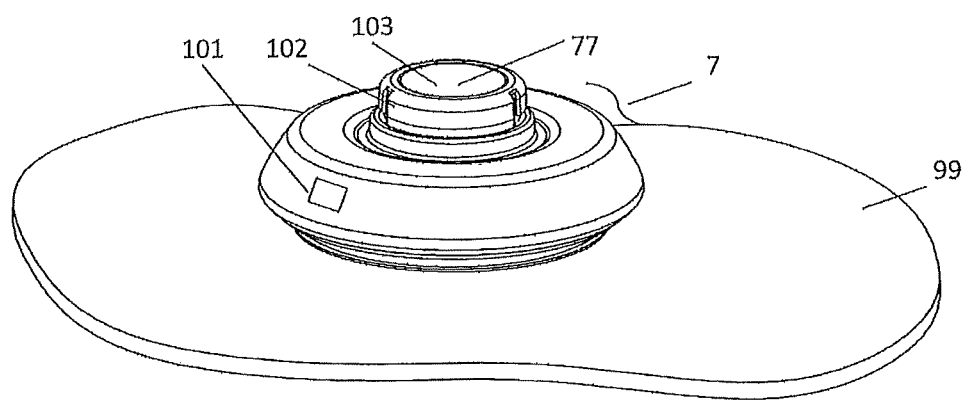
FIG. 8 is a perspective view of the injection device attached to the skin with the safety device removed and the button up in a pre-fire state.
Figure 9:
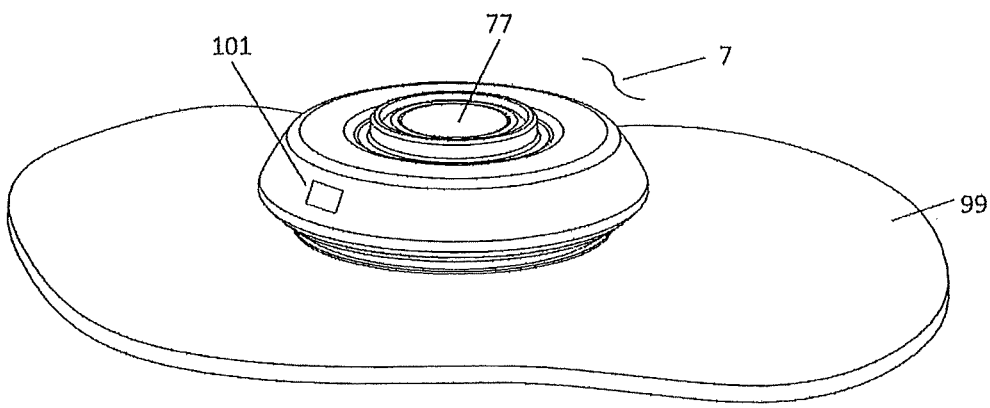
FIG. 9 is a perspective view of the injection device attached to the skin with the safety device removed and the button down in a fired state.

Referring to FIGS. 7-9, after the injection device 7 is placed against or adhered to the skin 99, a safety mechanism or lock-out mechanism may be automatically released and the injection device 7 is ready to fire (inject). In other words, the injection device 7 is prevented from being actuated (it is locked out) until it is placed against the skin. Alternatively, the user may manually remove a safety 100 such as a safety pin, safety sleeve, or collar to release the injection device to be ready to fire (inject). The injection device 7 preferably cannot be fired until the safety mechanism 100 is released. The safety mechanism 100 may be passive or active and manually triggered by the user or automatically triggered by the injection device 7.

Referring to FIGS. 7-9, the injection device 7 may use an actuator or button 77 and a visual indicator 101 in combination to define the state of the injection device 7 after it has been removed from the transfer apparatus. For example, when the button 77 is in the up position and the indicator 101 has one color such as but not limited to green, this may indicate that the injection device 7 is ready to start the injection. Additionally, the button 77 may have a side wall 102 that is a different color from its top 103. When the button 77 is depressed, the user cannot see the sidewall 102 of the button 77; this may indicate that the injection device 7 is in use. The injection device 7 may alert the user when the injection of the drug is completed. This alert could be in the form of visual indicators, audible sounds, mechanical movements or a combination. The button 77 is ideally designed to give the user audible, visual and tactile feedback when the button 77 'pops up' into the locked-out position. The injection device 7 may indicate to the user that it is has completed dispensing and the full dose has been delivered to the patient with the button 77 in the up position and indicator window 101 showing the injection device is empty. For example, when the button 77 is in the up position and indicator 101 shows a different color such as but not limited to red, this may indicate that the injection device 7 has completed the injection.

Figure 10:
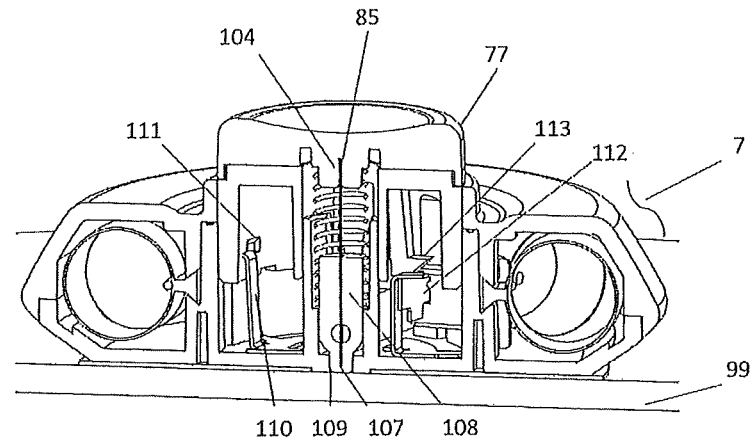
FIG. 10 is a cross-section view of the injection device attached to the skin with the button up in a pre-fire state.
Figure 11:
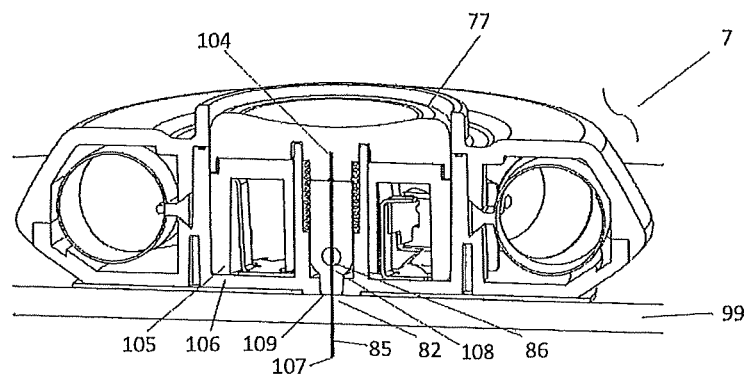
FIG. 11 is a cross-section view of the injection device attached to the skin with button down in a first fired state.
Figure 12:
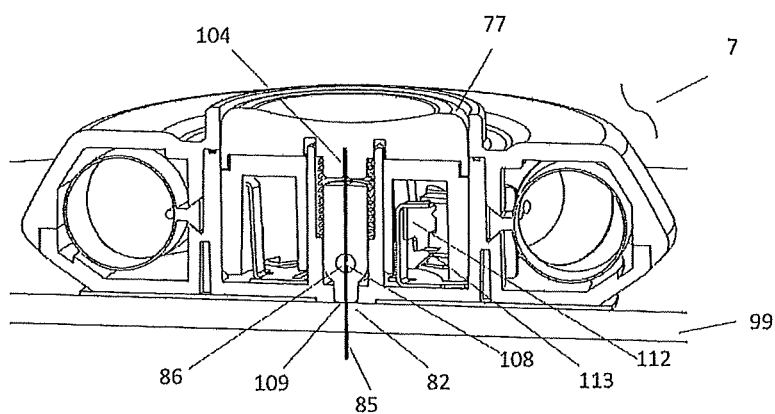
FIG. 12 is a cross-section view of the injection device attached to the skin with button down in a dispense state.

Referring to FIGS. 10-12, the injection device 7 may have an actuator or button 77 that the user depresses on the injection device 7 to start the injection. The button 77 may be configured to be an on/off switch, i.e., to only have two states, open and closed such as a light switch. This may prevent the user from pushing the button 77 half way and not actuating the injection device 7. Once activated, this 'light switch' type button 77 would insert the needle 85 rapidly into the skin 99, independent of the user manipulation of the button 77. Alternatively, the button 77 could have a continuous motion, allowing the user to slowly insert the needle 85 into skin 99. The button 77 may preferably be directly coupled to the needle 85 by using adhesive 104 creating a button 77 and needle 85.

Figure 31:
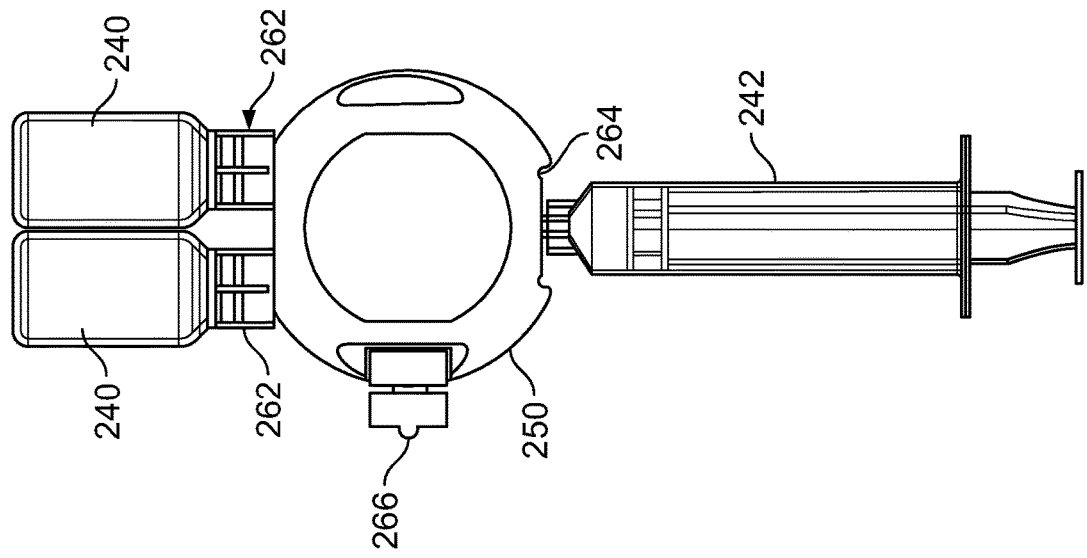
FIG. 31 is a bottom view of the system of FIG. 29.
Figure 30:
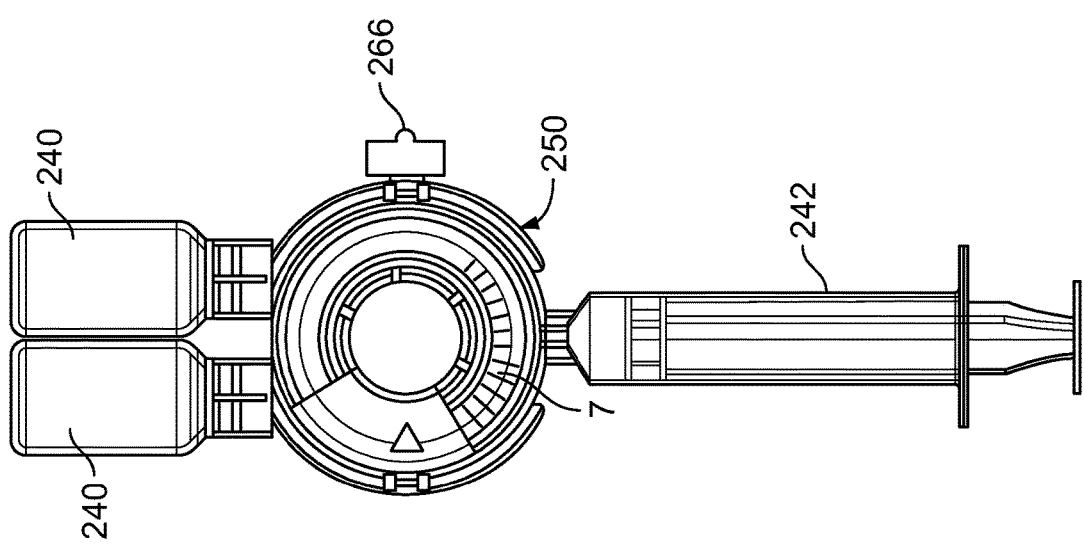
FIG. 30 is a top view of the system of FIG. 29.

Referring to FIGS. 10-12, the injection device 7 may have a needle 85 travel into the skin 99, upon actuation of the button 77 that initially goes to a first position or depth as shown in FIG. 30 and retracts slightly to a second position of depth preferably automatically as shown in FIG. 31. The first depth shown in FIG. 30 is achieved from over travel of the button 77 during actuation. The first depth may be controlled by features 105 in the button 77 in direct contact with the base 106 of the injection device 7. The final depth of the needle 85 is suitable for subcutaneous injections. Alternatively, the final depth of the needle 85 may be reduced for intradermal injections. Alternatively, the final depth of the needle 85 may be increased for intramuscular injections. Upon reaching the first depth, the needle 85 retracts back to a second depth as shown in FIG. 31. The retraction distance of the needle to the second depth is in the range of 0.1-2 mm. This retraction feature is preferable to prevent the needle 85 from being blocked by tissue during the initial insertion process. This tissue blockage could require a very high pressure to overcome and prevent the injection device 7 from delivering the drug. The retraction of the needle 85 from the first position to a second position creates an open pocket ahead of the needle tip 107 allowing reduced pressure for initiation of flow of drug from the needle 85. This reduced pressure for initiation of the flow of drug from the needle is preferable for the injection device 7 to maintain a relatively constant pressure during injection.

Referring to FIGS. 10-12, the injection device 7 may include a needle 85 with a side hole 108. As shown in FIG. 31, once the button 77 on the injection device 7 is fully depressed, the needle 85 will be fully inserted into the skin 99 through the dispense port 82 and the injection device 7 will begin dispensing of the injectable. Until the button 77 is fully depressed, the side-hole 108 and therefore the internal lumen of the needle 85 is not in communication with the fluid channel 86 of the dispense port 82. Both the side-hole 108 and needle-tip 107 are retained within a septum 109. With the side-hole 108 and needle-tip 107 being retained within the septum 109, the entire drug path is kept sterile until the time of use. When the button 77 is fully depressed and the needle 85 is in the dispense position, a side hole 108 in the needle 85 is in communication with the fluid channel 86 of the dispense port 82 and the injection of the liquid begins.

Referring to FIGS. 10-12, the septum 109 provides the advantage of sealing the needle tip 107 as well as the side hole 108 from the injectable before and after dispense. Sealing the needle tip 107 and the side hole 108 of the needle 85 at the end of the injection has a particular advantage to prevent dripping of injectable from the injection device 7 after end of dispense and/or after it is removed from the skin surface. It also prevents contaminates from entering the hollow needle prior to being actuated into the skin. The septum 109 may be made of any suitable material to allow for sealing once the needle 85 has punctured it. The material composition of septum 109 may preferably be silicone. Alternatively, the material composition of the septum may also be a blend of different materials including but not limited to bromobutyl, chlorobutyl, isoprene, polyisoprene, SBR, polybudtadiene, EPDM, natural rubber and silicone. Alternatively, the fluid pathway 86 including the dispense port 82 could be a rigid plastic with a silicone injected over mold to produce the septum previously described.

Referring to FIGS. 10-12, the septum 109 at the dispense port 82 could protrude slightly from the underneath surface into the skin surface 99 of the injection device 7 to provide for pressure on the skin surface 99 at the injection site. This pressure on the skin surface 99 by the dispense port 82 after the needle is retracted could eliminate injectable from coming out of the injection site commonly referred to as blow-back.

Figure 29:
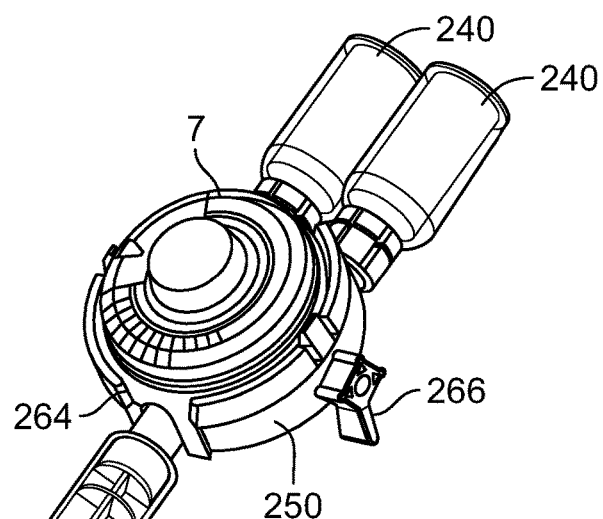
FIG. 29 is a perspective view of an injection system including an injection device generally as shown in the above FIGS. 1-20, a transfer device as in FIGS. 21-28 temporarily coupled thereto, a pair of standard vials and a standard syringe.

Referring to FIGS. 10-12, the injection device 7 may include a set of spring tabs 110 that interface with the button 77 to perform locking functions. A spring tab 110 is biased to lock into an undercut 111 in the button 77 to keep the button 77 in a first up position or pre-fire position as shown in FIG. 29. The geometry of the undercut 111 and spring tab 110 help to produce the light switch actuation force described previously. This light switch actuation is accomplished by the translation of the button 77 relative to the spring tab 110 and the geometry of the mating undercut 111 surfaces.

Referring to FIGS. 10-12, the injection device 7 may include a spring tab 112 that interact with the button 77 in the injection device 7 to perform locking functions such that when the button 77 is actuated to the first depth and retracts slightly back to the second depth or dispense position, undercut features 113 in the button 77 allow a spring tab 112 to hold the button 77 in the dispense position until the injection device 7 has completed dispensing.

Figure 13:
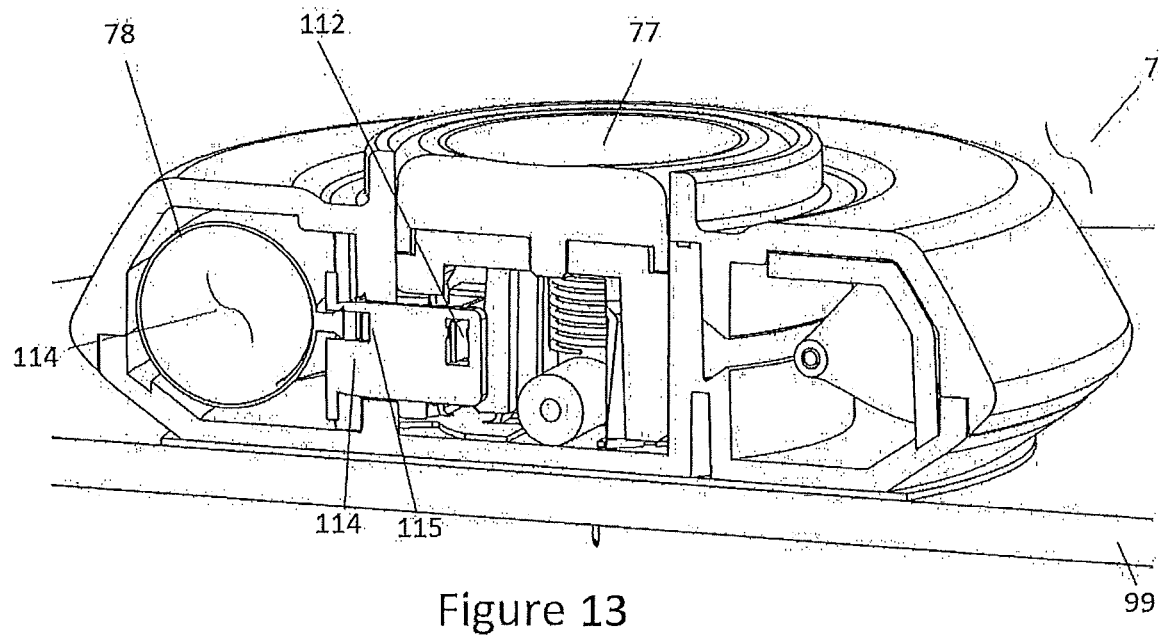
FIG. 13 is a cross-section view of the injection device attached to the skin showing the end of delivery indicator not triggered.
Figure 14:
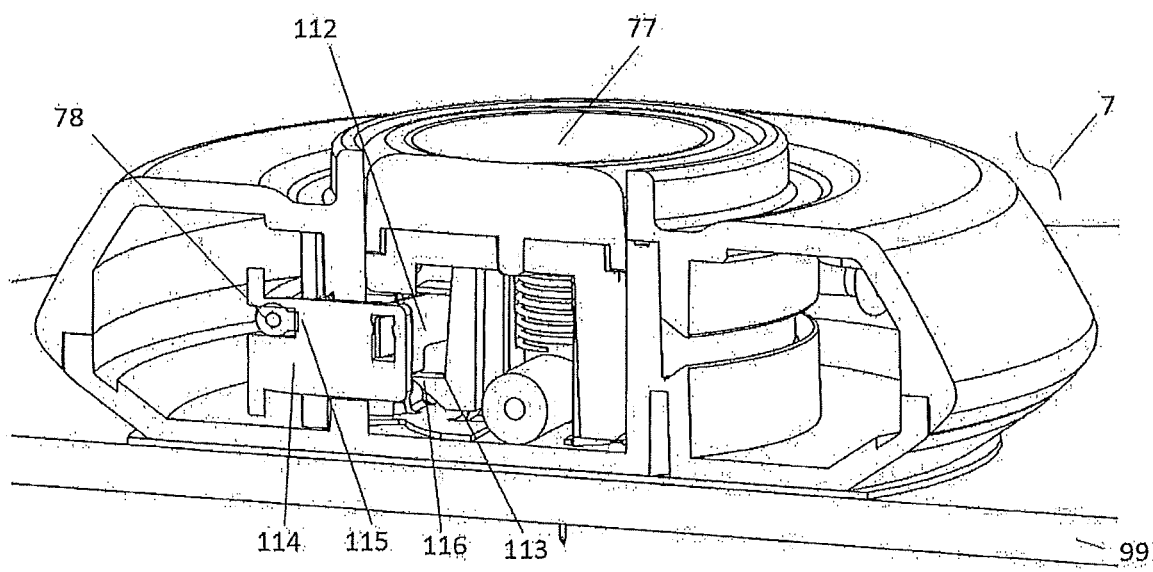
FIG. 14 is a cross-section view of the injection device attached to the skin showing the end of delivery indicator triggered.
Figure 32:
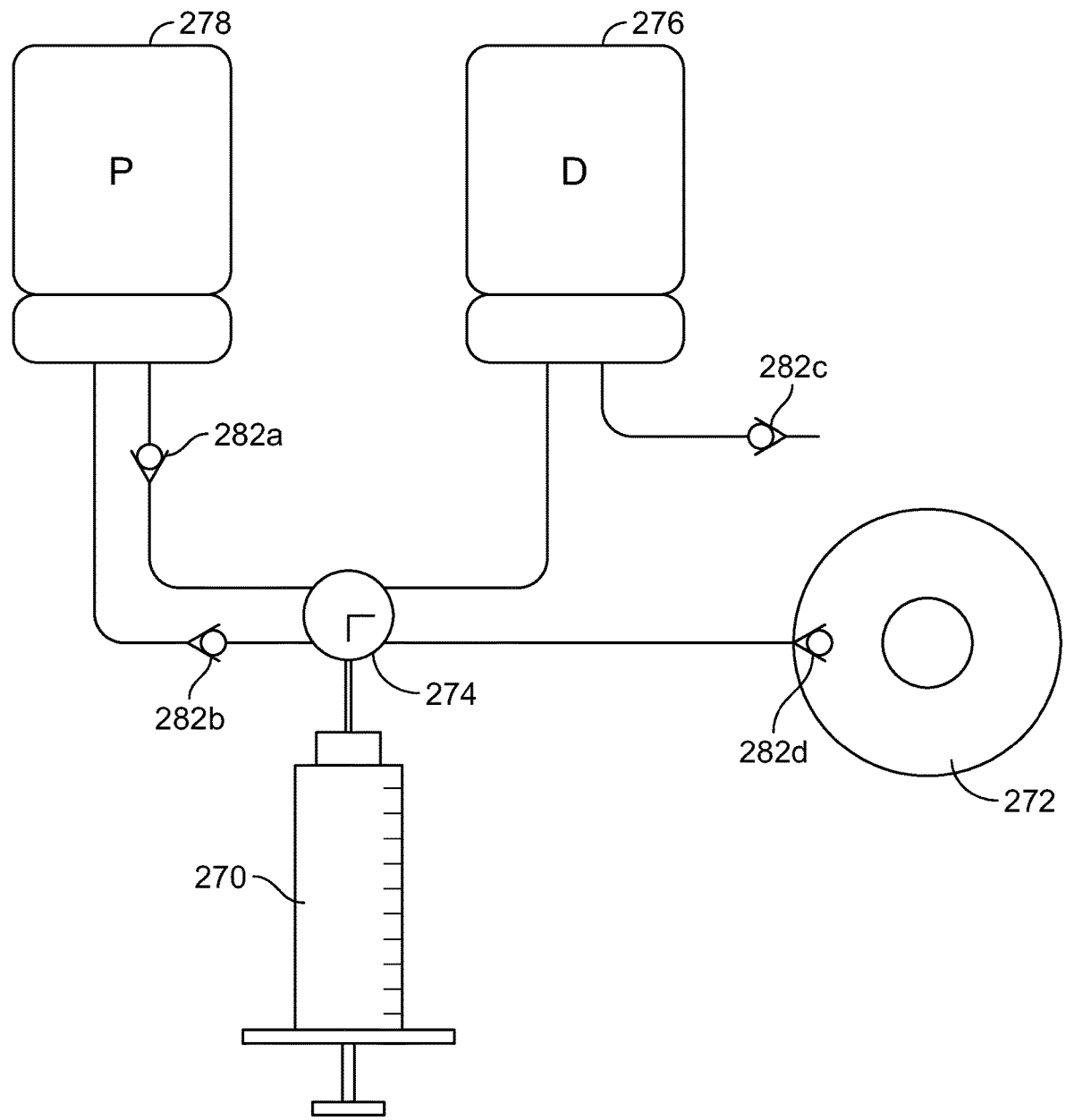
FIG. 32 is a schematic of the flow arrangement of the system of FIG. 29 in a first valve position.
Figure 33:
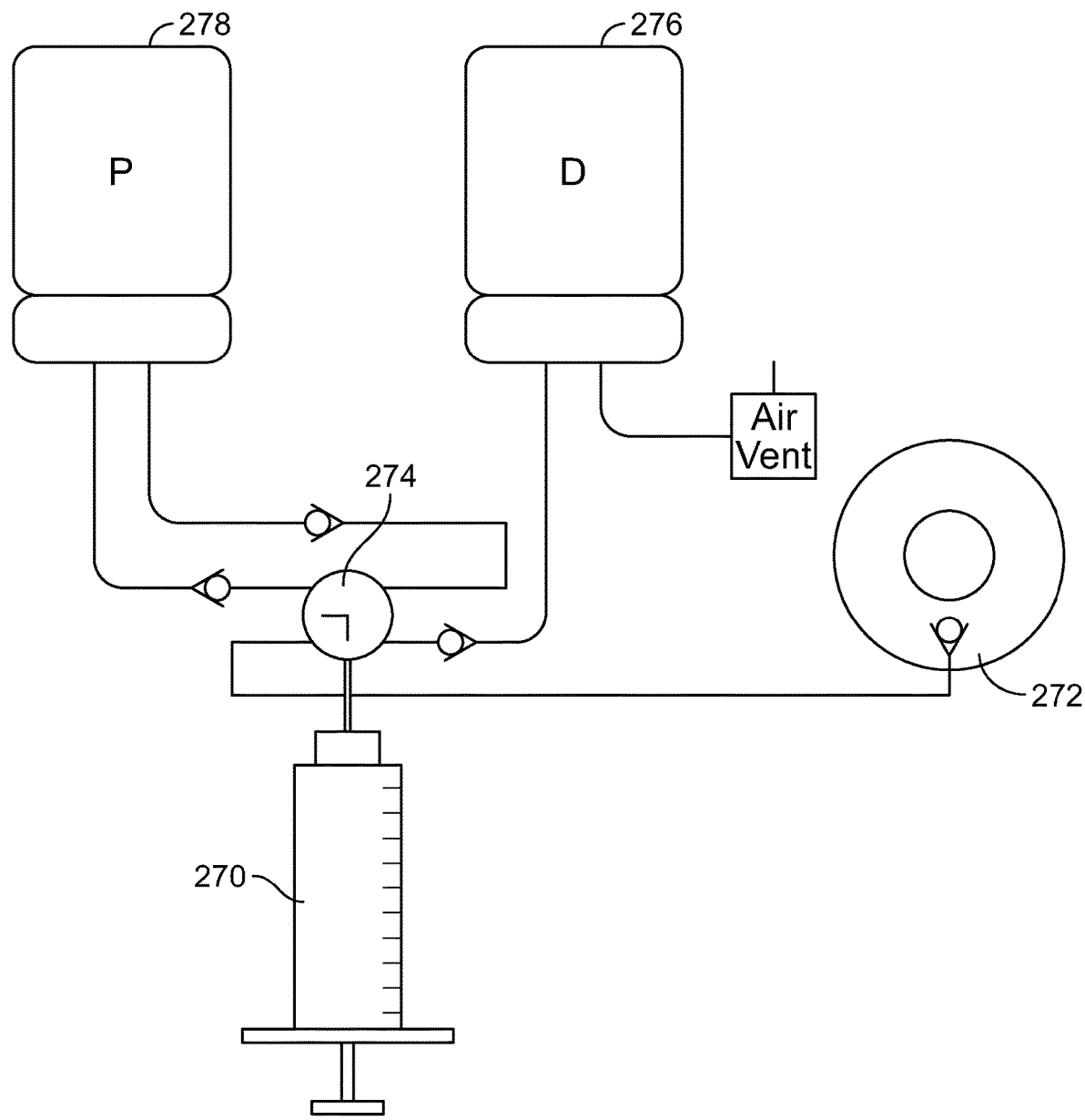
FIG. 33 is a schematic of the flow arrangement of the system of FIG. 29 in a second valve position.

Referring to FIGS. 13-14, the injection device 7 may include an end of delivery indication or empty indicator 114 to sense when all of the fluid 79 has been expelled from the expandable member 78 and the injection device 7 has completed dispensing. The empty indicator 114 may be configured with a slot or other opening 115 to slide over the expandable member 78 at the exit port when the expandable member 78 is in a deflated state after all of the fluid has been expelled. There may be two states of the empty indicator. As shown in FIG. 32, the empty indicator may be in a first position or deflected-out state when the expandable member 78 is full with fluid 79 at that section and is not contained within the slot or opening 115. This first position would translate to a non-empty state of the expandable member 78 when the diameter of the expandable member 78 is larger than its minimum due to residual fluid 79 contained within. As shown in FIG. 33, the empty indicator 114 may be in a second position or deflected-in state when the expandable member 78 is partially or fully contained within the slot or opening 115. This second position would translate to an empty state of the expandable member 78 when the diameter is at a minimum.

Figure 34:
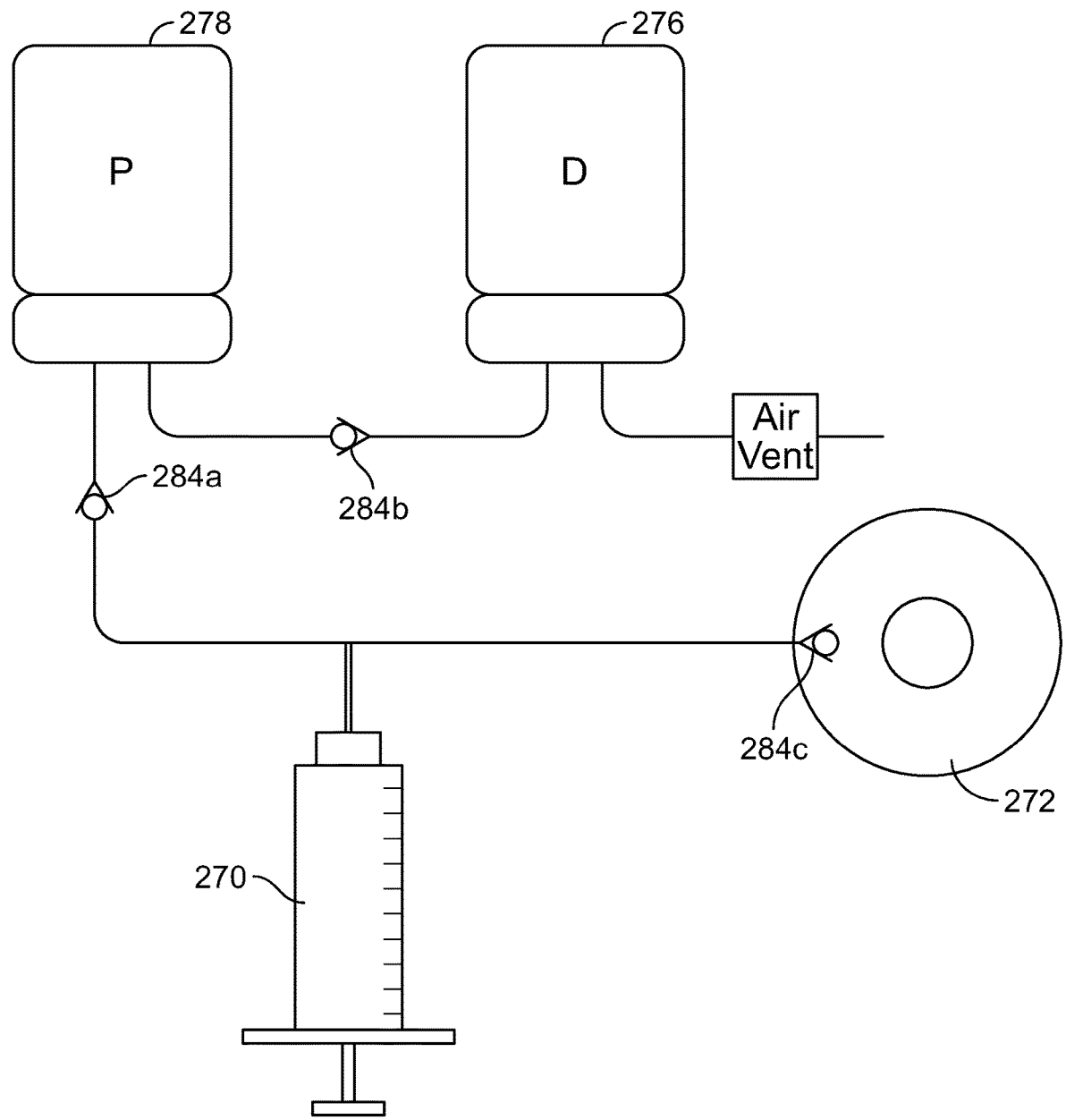
FIG. 34 is a schematic of an alternative flow arrangement of the system of FIG. 29.

Referring to FIGS. 13-14, the injection device 7 may include an automatic needle retraction mechanism at the end of dispense. This mechanism includes a direct coupling between a spring tab 112, button undercut feature 113 and the empty indicator 114, all previously mentioned. When the expandable member 78 is filled with injectable 79 and the button 77 is depressed from a first pre-fire position to a second dispense position as shown in FIG. 33, undercut features 113 in the button 77 allow a spring tab 112 to hold the button 77 in the dispense position until the injection device 7 has completed dispensing. This spring tab 112 may also be directly coupled to the empty indicator 114 which is naturally in the first position or deflected-out state. The motion of depressing the button 77 to a second position or dispense position allows a post feature 116 in the button 77 to provide a bias or pre-tension on the spring tab 112 to urge the empty indicator 114 to its second position or deflected-in state. However, since the expandable member 78 is initially full with injectable 79 at a large diameter, the empty indicator 114 cannot move to the second position or deflected-in state as shown in FIG. 32. After the button 77 is depressed, the fluid 79 starts to expel out of the expandable member 78 through the needle as previously mentioned. Once the expandable member 78 has expelled all of the fluid 79 and is at a minimum diameter, the empty indicator 114 (under pretension from the spring tab 112) will move to the second position or deflected-in state as shown in FIG. 33. The spring tab 112 directly coupled to the empty indicator 114 also moves with the empty indicator 114. This movement releases the spring tab 112 from the undercut feature 113 in the button 77 to allow the button 77 (and needle) to move up to a final position or post fire position after the dispense is completed as shown in FIG. 34.

Figure 15:
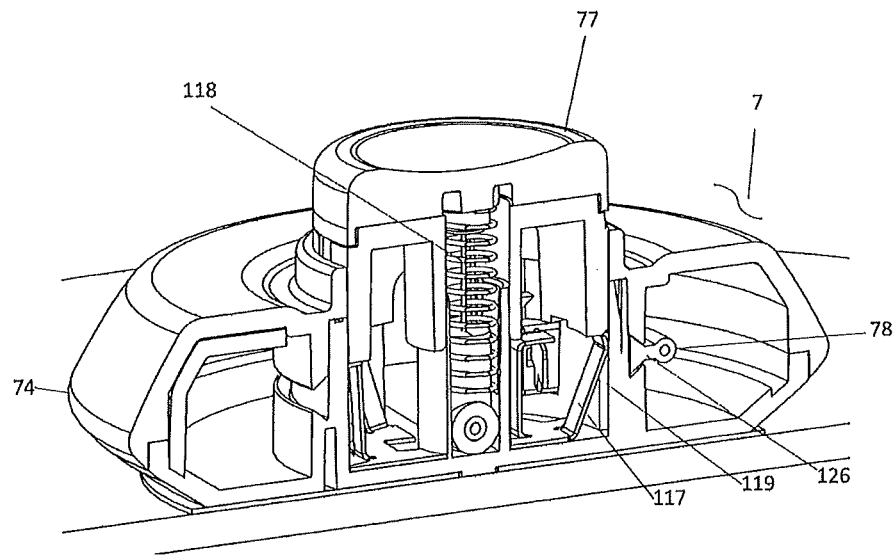
FIG. 15 is a cross-section view of the injection device attached to the skin with button locked up in a post-fired state.

Referring to FIG. 15, lock out spring tabs 117 may also interact with the button 77 in the injection device 7 to perform locking functions such that when the injection is complete the button 77 is released, and the button 77 is urged up by the return spring 118 to a final up position or post-fire position. The button height 77 relative to the top of the injection device 7 in the final up position or post-fire position (shown in FIG. 34) may be higher than the pre-firing position (shown in FIG. 29). The end of the lock out spring tabs 117 move out to the outer diameter surface 119 of the button 77 within the outer housing 74 to lock the button 77 in the up position or post-fire position and prevent the button 77 from being actuated again.

Referring to FIG. 15, the injection device 7 may include a return spring 118 that interacts with the button 77 to provide a bias to the button 77 into a first up position or pre-fire position. When the button is actuated down to a second depth or dispense position, the return spring 118 is compressed causing more of a bias or preload. At the end of the dispense period, the button 77 is unlocked from the second depth or dispense position (shown in FIG. 31) to move up to a final position or post fire position after the dispense is completed as previously mentioned. It is the bias of the return spring 118 that forces the button 77 up to a final position or post-fire position.

Figure 16:
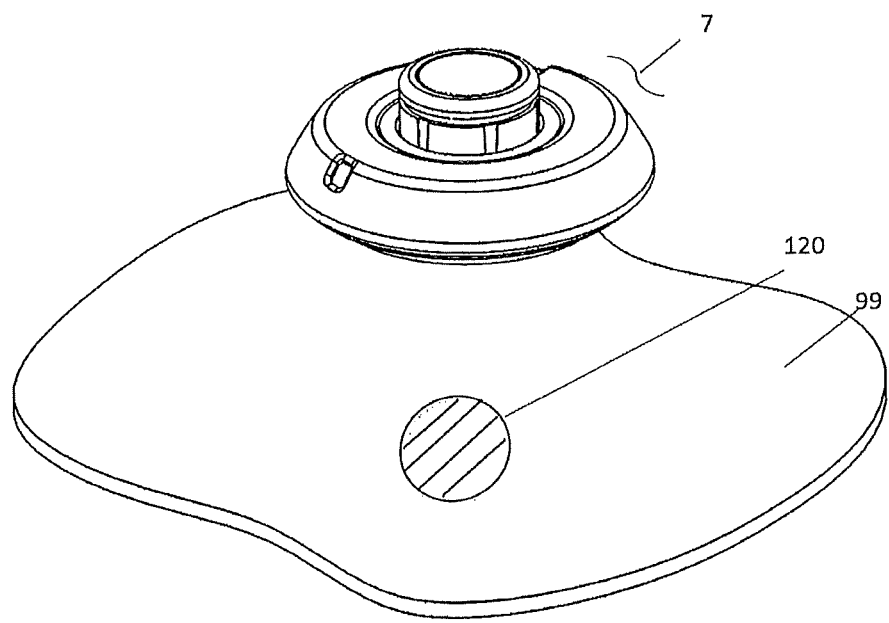
FIG. 16 is a perspective view of the injection device removed from the skin with the bandage remaining on the skin.
Figure 17:
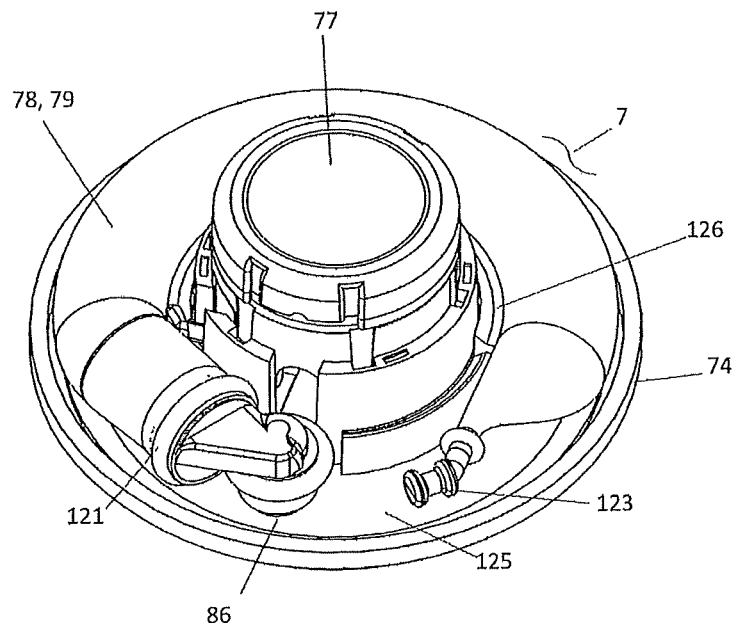
FIG. 17 is a perspective view of the injection device with the top housing removed in a filled state.
Figure 18:
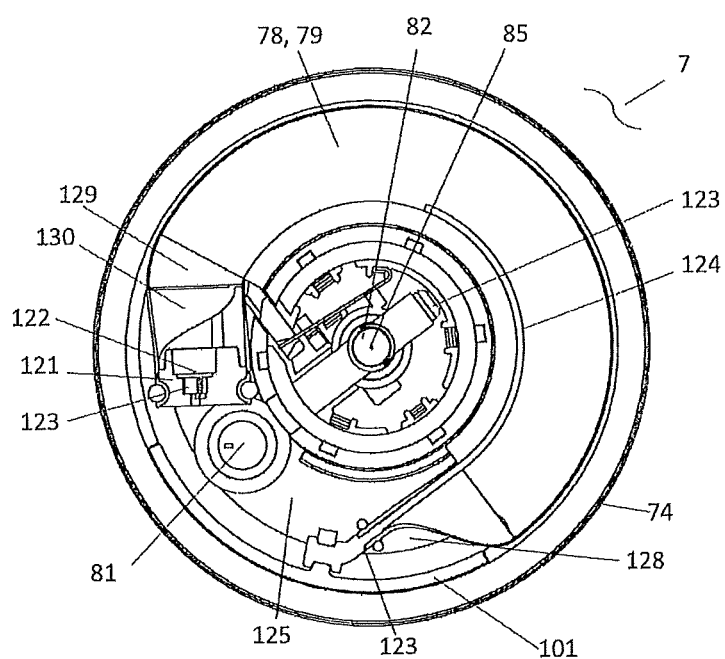
FIG. 18 is a top view of the injection device shown in FIG. 17.
Figure 19:
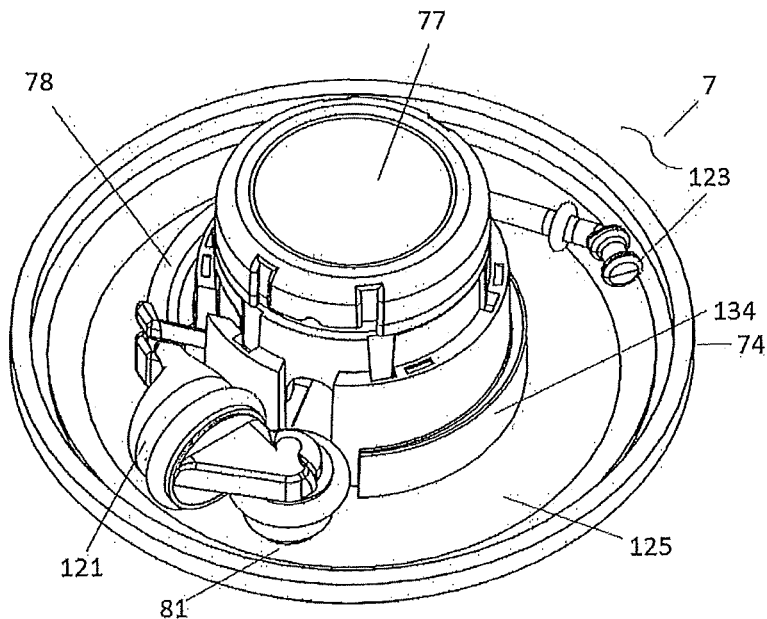
FIG. 19 is a perspective view of the injection device with the top housing removed in an empty state.
Figure 20:
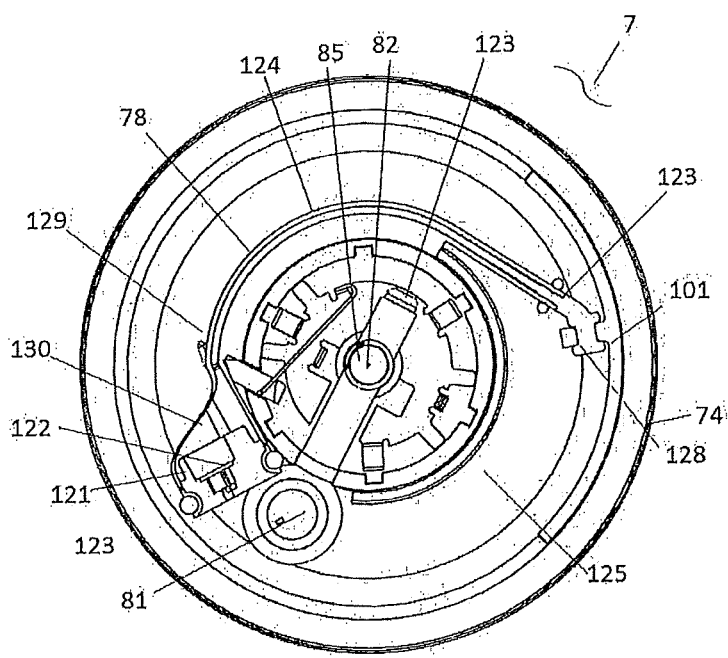
FIG. 20 is a top view of the injection device shown in FIG. 19.
Figure 21:
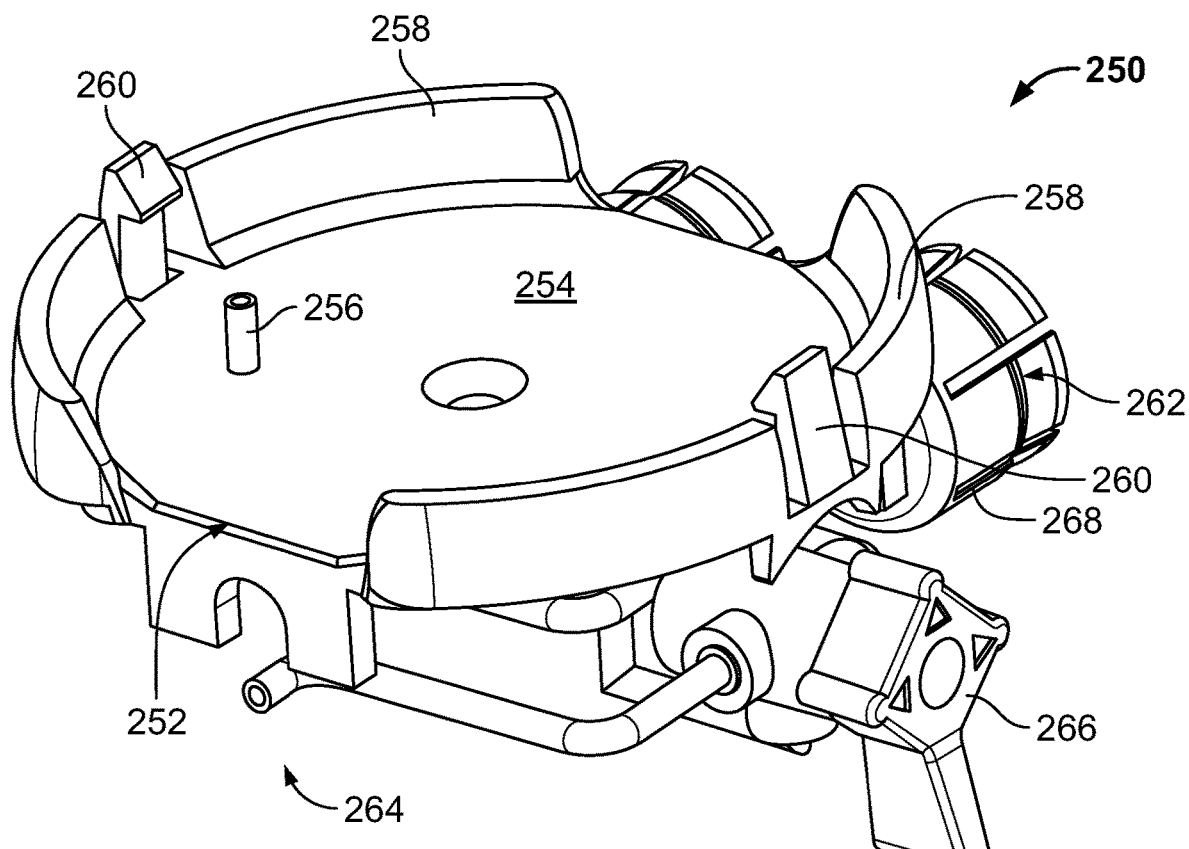
FIG. 21 is a perspective view of a transfer device for temporary coupling to an injection device such as the device shown in the figures above for manipulating/mixing/transferring an injectable from a plurality of vials into the injection device.

Referring to FIG. 15-16, upon removal of the injection device 7 from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

Referring to FIG. 16, upon removal of the injection device 7 from the skin 35, a bandage 120 may release from the injection device 7 and remain on the skin surface 35. This can be affected by using an adhesive on the bandage portion that more strongly attaches the bandage to the skin than the adhesive that attaches the bandage to the injection device 7. Thus when the housing is lifted from the skin, the bandage 120 remains in place over the injection site as described in U.S. Pat. No. 7,637,891 and U.S. patent application Ser. No. 12/630,996, filed Dec. 4, 2009 incorporated by reference herein.

Referring to FIGS. 17-20, the injection device 7 may preferably include a manifold 121 that assembles to both the expandable member 78 and the filling port 81 and dispensing ports 82, and provides direct fluid communication between the expandable member 78 and the filling 81 and dispensing 82 ports of the injection device 7. The manifold 121 may be configured on the end that assembles to the expandable member 78 to be large in diameter to facilitate filling and expelling all of the fluid 79 out of the expandable member 78 as previously discussed. The manifold 121 may preferably include internal passageways 122 to allow for fluid flow in and out of the expandable member 78. The manifold 121 may be configured with a filter 123 in the injectable fluid pathway 122 for filtering the injectable 79 to remove particulate before and after it is introduced into the expandable member 78. The filter 123 may be a membrane, depth filter or other suitable filtration media that is of sufficiently small pore size or effective pore size to remove objectionable particulate, which may include but not be limited to undissolved injectable 79 in those situations where the injectable 79 is reconstituted by the transfer apparatus. The manifold 121 may also be configured with a filter 123 for the removal or air. Such an air remover filter 123 may include a bubble trap, air gap of other configuration in the injectable fluid pathway 122 that removes air from the injectable fluid pathway 122 before it is introduced into the expandable member 78. This air remover filter 123 may be configured with a hydrophobic filter or a combination of hydrophobic and hydrophilic filters. A hydrophobic filter would allow for the venting of air from the transfer apparatus but not the passage of liquid. A hydrophilic filter would allow the passage of liquid but not the passage of particulate or air. The air remover filter 123 may also have check valves to allow for venting of trapped air. Alternately, the air remover and filters 123 may be located at any point in the fluid pathway from the filling port 81 to the needle 85. For example, the most downstream point in the fluid pathway is the distal end 128 of the expandable member 78. An internal mandrel 124 may be connected to distal end 128 of the expandable member 78. An air remover or filter 123 may be integrated into this downstream point to allow for venting of trapped air during filling of the injection device 7. Furthermore, the mandrel 124 could include a slot along its length that is in communication with the downstream filter 123 to aid in the venting of air during the filling process.

Referring to FIGS. 17-20, the injection device 7 may include a resilient expandable member 78 such as an elastomeric balloon or bladder. The material composition of expandable member 78 may preferably be silicone. Alternatively, the material composition of the expandable member 78 may also be a blend of different materials including but not limited to bromobutyl, chlorobutyl, isoprene, polyisoprene, SBR, polybudtadiene, EPDM, natural rubber and silicone. In addition, the expandable member 78 may be coated to improve their surface properties. Coatings may include parylene, silicone, Teflon and fluorine gas treatments. Alternatively, the expandable member 78 may be made from a thermoplastic elastomer.

Referring to FIGS. 17-20, the injection device 7 may include a resilient expandable member 78 which the injectable 79 is transferred under pressure. This causes the expandable member 78 to enlarge and the resilience of the expandable member 78 creates a pressure which tends to expel the injectable 79. The pressure chamber of the transfer apparatus described previously (or such other pump or pressurizing means as may be employed in the transfer apparatus) transfers the injectable 79 to the injection device 7 under pressure. Introducing the injectable 79 into the expandable member 78 under pressure causes it to stretch and expand both in diameter and length. An example of this would be blowing up a long, skinny balloon. The volume range of the injection device 7 may be 0.5 to 30 milliliter. When expanded, the resilient expandable member 78 exerts an expulsion pressure in the range of 1 to 200 psi on the injectable 79 contained in the expandable member 78 so that the injection device 7 is ready to administer the injectable 79 automatically when triggered by the user by depression of the button as previously described.

TRANSFER DEVICE

FIGS. 21-34 relate to an embodiment of a transfer device 250 particularly suited for injectables that require reconstitution or dilution. This transfer device includes two vial adapters and a corresponding flow path arrangement described below. As seen in FIG. 31, this transfer device 250 includes a base 252 upon which the injection device 7 rests when coupled thereto. The base forms a support surface 254 from which a fluid transfer port 254 projects for insertion into the filling port 81 of the injection device. Raised peripheral walls 258 extend upwardly from the support surface, and together they define a nesting or docking site for receiving the injection device.

The transfer device may be made of one-piece molded plastic construction for low cost disposability. Alternatively, one or more features of the transfer device may be separately formed and assembled together to provide the complete transfer device.

The injection device may be temporarily held in the coupled position on the transfer device by opposed flexible hooks 260 that flex outwardly to receive the injection device and hook over the peripheral edge of the disc-shaped injection device to removably retain it on the transfer device. Alternatively or additionally, a harness arrangement may be used for temporarily coupling the transfer device to the injection device. More specifically, to hold the transfer device temporarily coupled to the injector, such a harness may be pivotally attached at one side of the base and can be pivoted over an associated injection device to straddle the base and injection device and hold the injection device in place. The free end of the harness may include a manually connectable and releasable clip or connector for securing the harness over an injection device and holding it against the base of the transfer device and for releasing the harness and the injection device when fluid transfer into the injection device is completed. To help avoid lateral shifting of the injection device when coupled to the transfer device, the harness may have an intermediate ring that extends around or circumscribes the actuator button of the injector.

The transfer device 250 includes a pair of vial adapters 262, a syringe adapter 264, a fluid flow control valve 266 and associated flow path segments.

The syringe adapter 264 may be optionally provided with a standard hollow female luer lock adapter (not shown) with standard dimensions designed to interfit with the usual standard male syringe luer port located at the discharge end of standard syringes. In such an embodiment, radial projections or ears of the luer connector cooperate with a threaded collar that is located around the male luer of the standard syringe so that relative rotation secures the male and female luer portions together and avoids accidental or premature disconnection.

Figure 22:
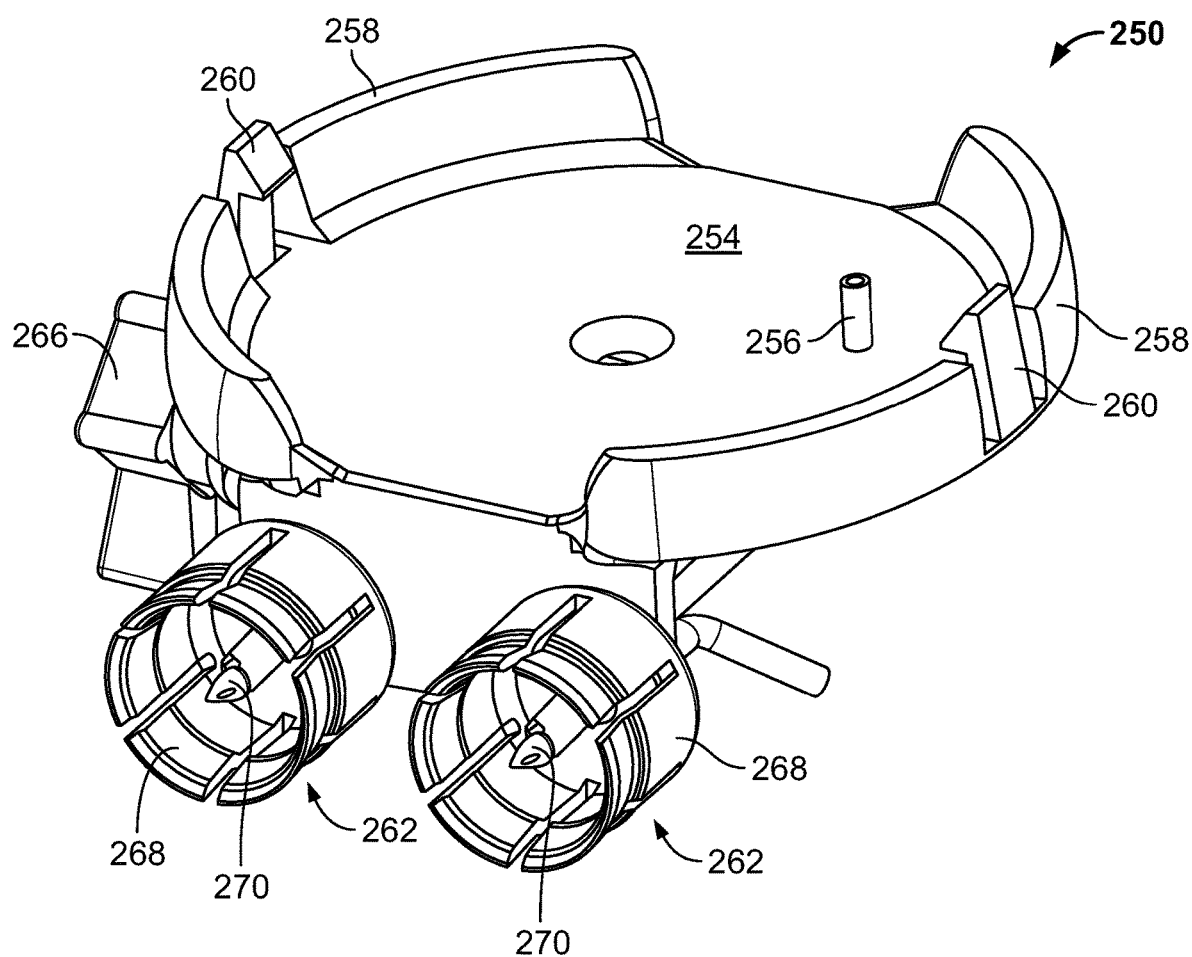
FIG. 22 is a perspective view of a transfer device of FIG. 21, taken from a different angle.
Figure 23:
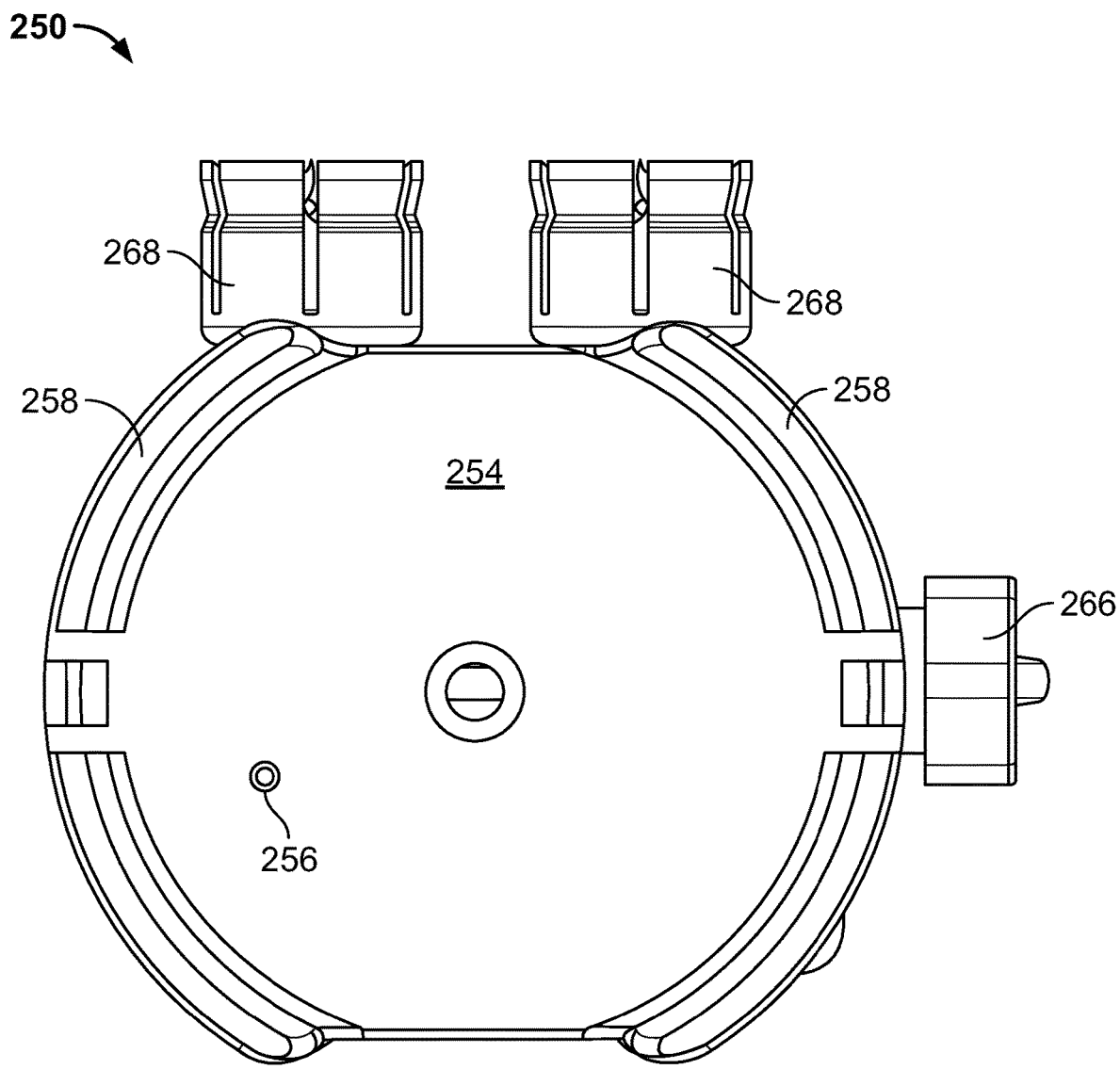
FIG. 23 is a top view of the transfer device of FIG. 21.
Figure 28:
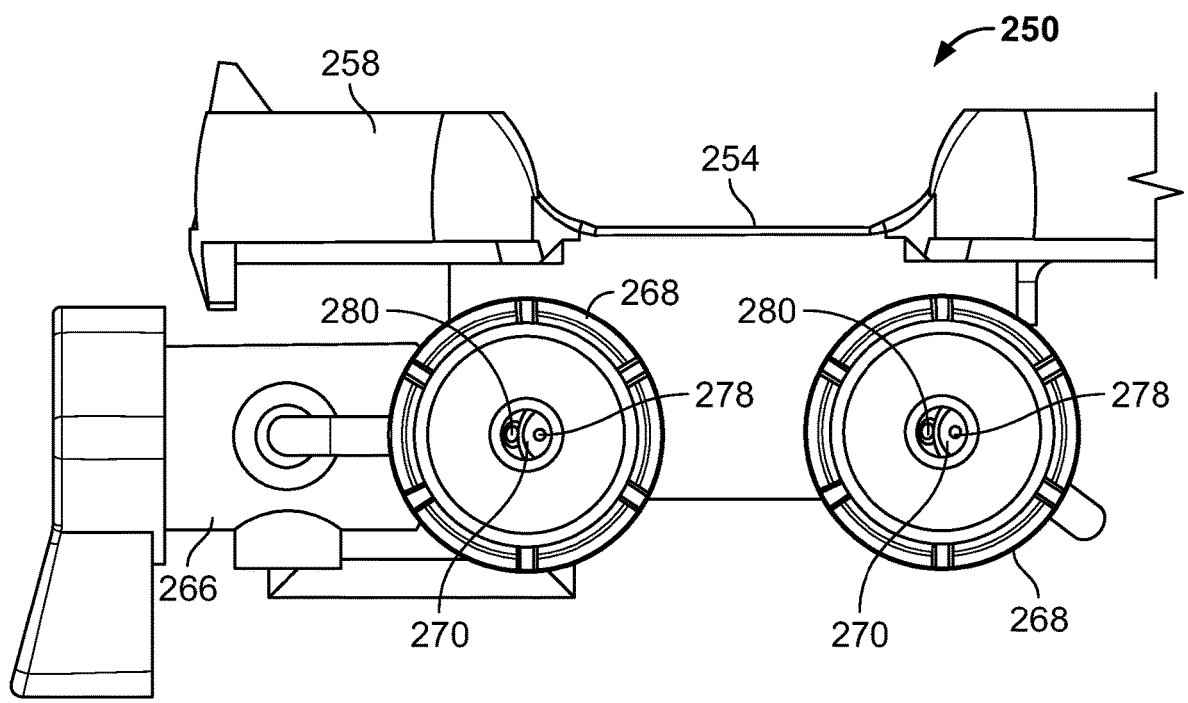
FIG. 28 is an end view of the transfer device of FIG. 21 looking directly at a pair of vial adapters.

Referring to FIG. 22, each vial adapter features an external collar 268, that is flared outwardly at the open end for guided reception of the end of a standard vial of injectable, and a hollow piercing pin or cannula 270 for piercing the septum that seals the open end of a standard medicine vial. Each vial adapter may include a venting feature that allows displacement air to enter or leave the vials and such a venting feature may, for example, be provided as an additional lumen in the piercing pin 270 or as an additional hollow piercing pin or cannula that is devoted to movement of venting air to and from the vial and vented to the atmosphere. FIG. 28, which is a view into the vial adapters 262 show piercing spikes, each with two lumen 278, 280—one for liquid introduction and withdrawal and one for venting.

Figure 24:
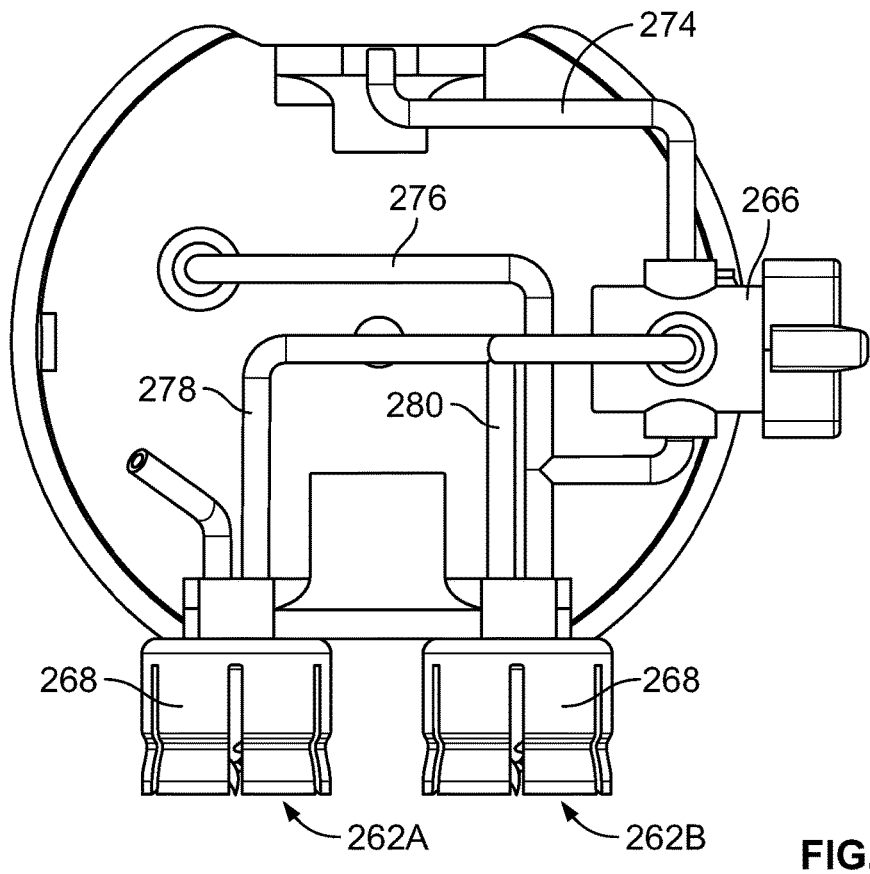
FIG. 24 is a bottom view of the transfer device of FIG. 21.
Figure 25:
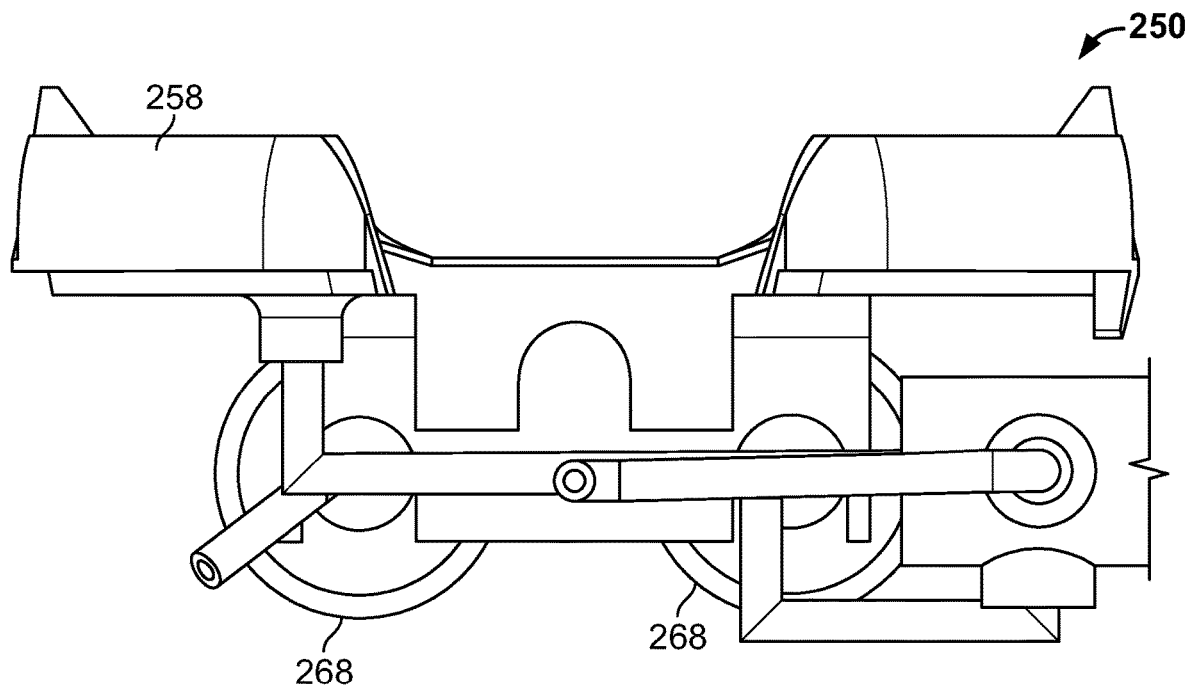
FIG. 25 is an end view of the transfer device of FIG. 21 looking directly at a syringe adapter, with portions removed.
Figure 26:
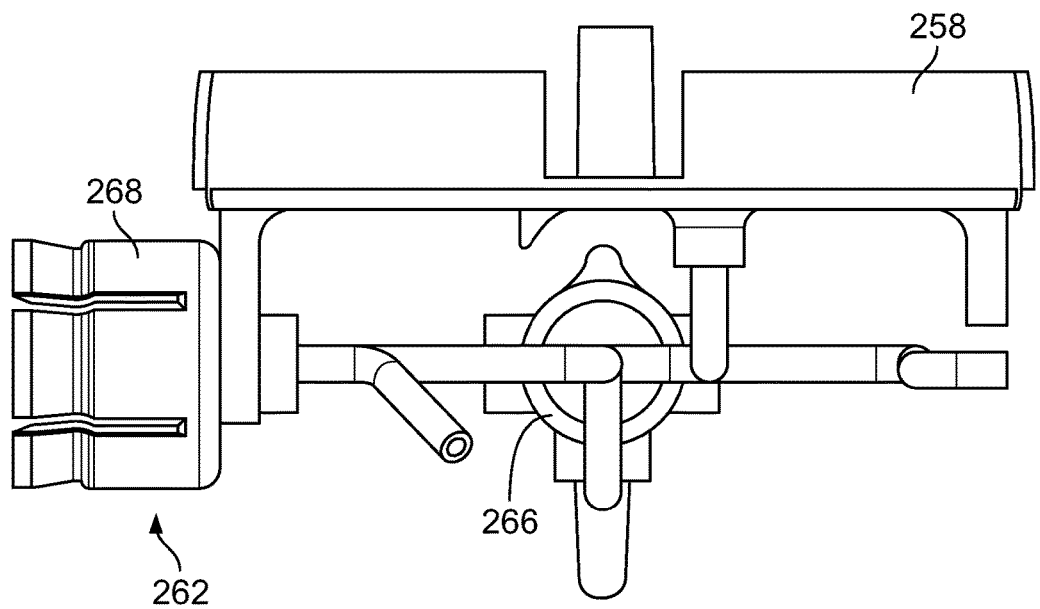
FIG. 26 is a side view of the transfer device of FIG. 21.
Figure 27:
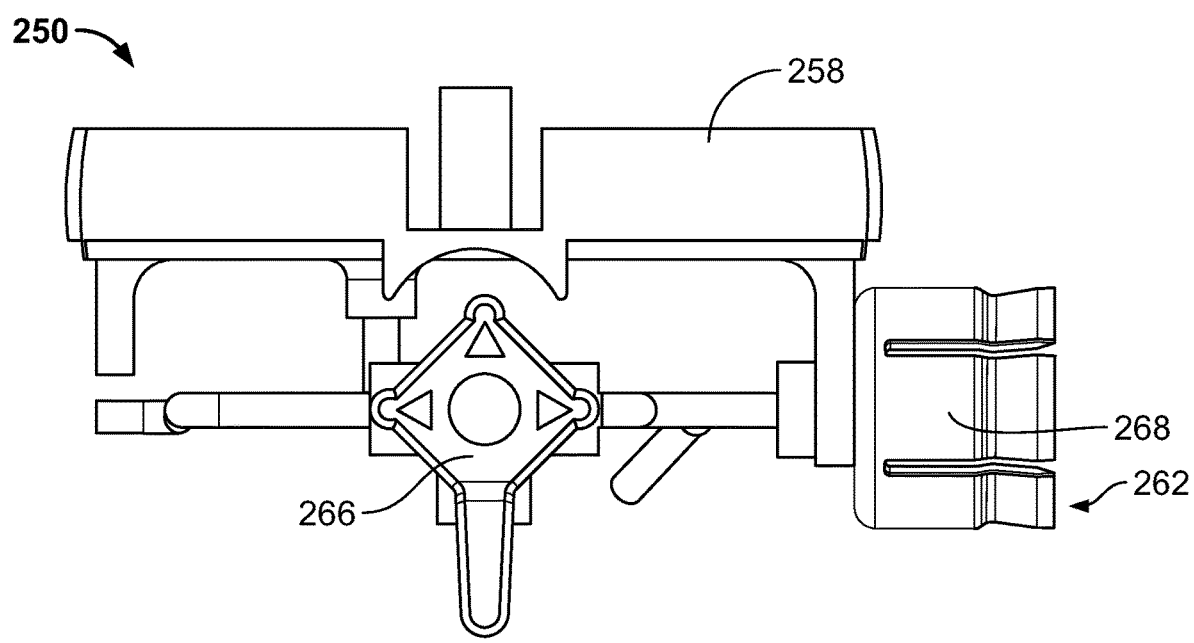
FIG. 27 is an opposite side view of the transfer device of FIG. 21.

One example of a fluid flow path arrangement for this transfer device is seen in FIG. 24, a view of the underside of the transfer device 250. As seen there, a fluid flow path segment 274, such as a length of plastic tubing, extends between flow control valve 266 and syringe adapter 264. Fluid flow path segment 276 extends between the flow control valve and the fluid transfer port 256. Fluid flow path segment 278 extends between the flow control valve and the diluent vial adapter 262A and fluid flow path segment 280 extends between the flow control valve and the injectable vial adapter 262B.

The fluid flow arrangement here allows the ready use of the transfer device when the injectable requires reconstitution or dilution. The injectable vial may be attached to one of the one of the vial adapters and the diluent used to reconstitute or dilute attached to the other vial adapter. After the diluent and injectable vials and the syringe are attached to the transfer device, the flow control valve is positioned to allow flow between the diluent vial adapter and the syringe. Retracting the syringe plunger draws diluent from the diluent vial into the syringe. The flow control valve is then repositioned to place the syringe and the injectable vial into flow communication and the diluent is injected into the injectable vial to reconstitute the injectable. As described earlier, reconstitution may be promoted by manually shaking the entire assembly and/or by cycling the syringe plunge back and forth to repeatedly withdraw fluid from and inject fluid into the injectable vial, causing agitation and mixing of the diluent and injectable. The reconstituted injectable is then collected into the syringe. These steps may be carried out before or after coupling of transfer device to the injection device 7, and may be repeated with additional injectable and diluent vials if necessary for increase dosage. If carried out prior to attachment of the injection device, the injection device will then be coupled to the transfer device and the valve repositioned again to place the syringe (which contains the reconstituted injectable) and fluid transfer port into fluid communication, and depression of the syringe plunger forces the reconstituted injectable through the fluid transfer port 256 and the filling port 81 into the injection device 7, expanding the resilient expandable member or bladder 78 and preparing the injection device for use.

The assembled two-vial system including the injection device 7, transfer device 250, a standard injectable-containing vial 240, standard diluent containing vial 240 and a standard syringe 242 is shown in FIGS. 39-41. The vials and/or syringe may be attached to the transfer device before or after the transfer device is secured to injector 7. This arrangement allows for user ease of reconstitution or dilution of the injectable and delivery into the injection device.

The device described above therefore provides a handheld reconstitution syringe transfer system to allow for a compact and efficient way to reconstitute lyophilized drug, remove the drug from a vial into a syringe then transfer the drug into the injector.

In basic principle, the user attaches the lyophilized drug and diluent vials to the assembly with the vial adapter(s). Each drug and diluent vial can have a capacity of 1-50 mL with neck finishes of 13-20 mm. The syringe capacity can be 1-50 mL. The injector capacity can be 1-50 mL.

The user can attach the lyophilized drug and diluent vial(s) to the vial adapter then attach it to the system. Alternatively, the vial adapter would be part of the system and the user inserts the vial(s) into the system.

The vial adapter(s) contain a spike to access the vial through the rubber stopper and has two fluid paths. A first vial adapter with one vented to atmosphere and the other connected to the fluid path. This allows for easy withdraw of the fluid from the vial without creating a vacuum. The other vial spike would allow for connection of two independent sources.

The syringe is connected to the other side for withdrawal of the fluid from each of the diluent vial and/or reconstituted vial and transfer of the fluid into the injector.

Once the vial(s) and syringe are attached to the system, the valve is positioned to State 1 creating a fluid path between the diluent vial and syringe and allowing from withdraw of the diluent into the syringe.

By pulling on the syringe plunger, fluid is withdrawn from the diluent vial into the syringe. The entire contents of the diluent vial can be removed or partial contents based on the patient's dose.

The user can attach multiple diluent vials to fill one syringe to get a necessary dose into the syringe.

The user then can switch the valve to State 2. This creates a fluid path from the filled syringe (with diluent) to the lyophilized vial.

In an alternative embodiment, the diluent comes in a prefilled syringe. In this case, the diluent can be directly transferred to the lyophilized vial. (This can also be accomplished in a single vial system).

The user can push on the plunger of the syringe transfer the contents of the syringe to the lyophilized vial.

In an alternative embodiment, the lyophilized vial is under vacuum. By insertion of the diluent vial and lyophilized vial, the vacuum in the lyophilized vial automatically pulls the diluent into the lyophilized vial.

Once the diluent is transferred to the lyophilized vial, the reconstitution process can begin.

The user can manually agitate the diluent/powder mixture until the powder is completely dissolved in solution.

The user can then pull back on the syringe to pull the entire contents of the mixed solution or a partial dose, depending on what was prescribed.

Prior to determining the final dose, there may be some air in the syringe. The user can prime the syringe by expelling the excess air in the syringe back into the vial.

Once the desired amount of fluid is removed from the vial and into the syringe, the valve is switched to State 3. This creates a fluid path between the filled syringe and the injector.

The user pushes on the plunger of the syringe to expel the contents of the syringe into the injector.

If air exists in the syringe during transfer, the system can filter air to prevent air from being transferred into the injector. A filter in the fluid path between the syringe and the injector can filter the air. This can be accomplished with a hydrophobic filter or combination of hydrophilic/hydrophobic filter.

The retaining harness or strap, if used, can be unlocked and the filled syringe can be removed from the system.

FIGS. 32 and 33 are schematic flow diagrams that show a dual vial system with a syringe 270, injection device 272 (OBDD), three way valve or stopcock 274, diluent vial 276 (D) and injectable vial 278 (P), which system also employs check valves 282a, 282b, 282c and 282d that limit flow to one direction only. FIG. 33 shows the valve 274 position for drawing diluent from the diluent vial into the syringe 270 and FIG. 33 shows the valve position after diluent has been drawn into the syringe for injecting the diluent from the syringe into the injectable vial. FIG. 34, also a flow schematic, shows a dual vial system but without a stopcock and relying on one-way valves 284a, 284b and 284c only to control flow. In this system, vacuum created by pulling back on the syringe plunger draws diluent from the diluent vial through the injectable vial and into the syringe 270. This system may find particular application for injectables that require dilution only or for injectables that readily reconstitute in the presence of diluent. The one-way valves only allow fluid flow in one direction through the system—from the diluent vial 276 (D) to the injectable vial 278 (P), from the injectable vial 278 (P) to the syringe 270, and from the syringe 270 into the injection device 272 (OBDD). The check valves may not be required in embodiments where the vacuum in the injectable vial is used to pull diluent into it. The check valves may be redundant.

Figure 35:
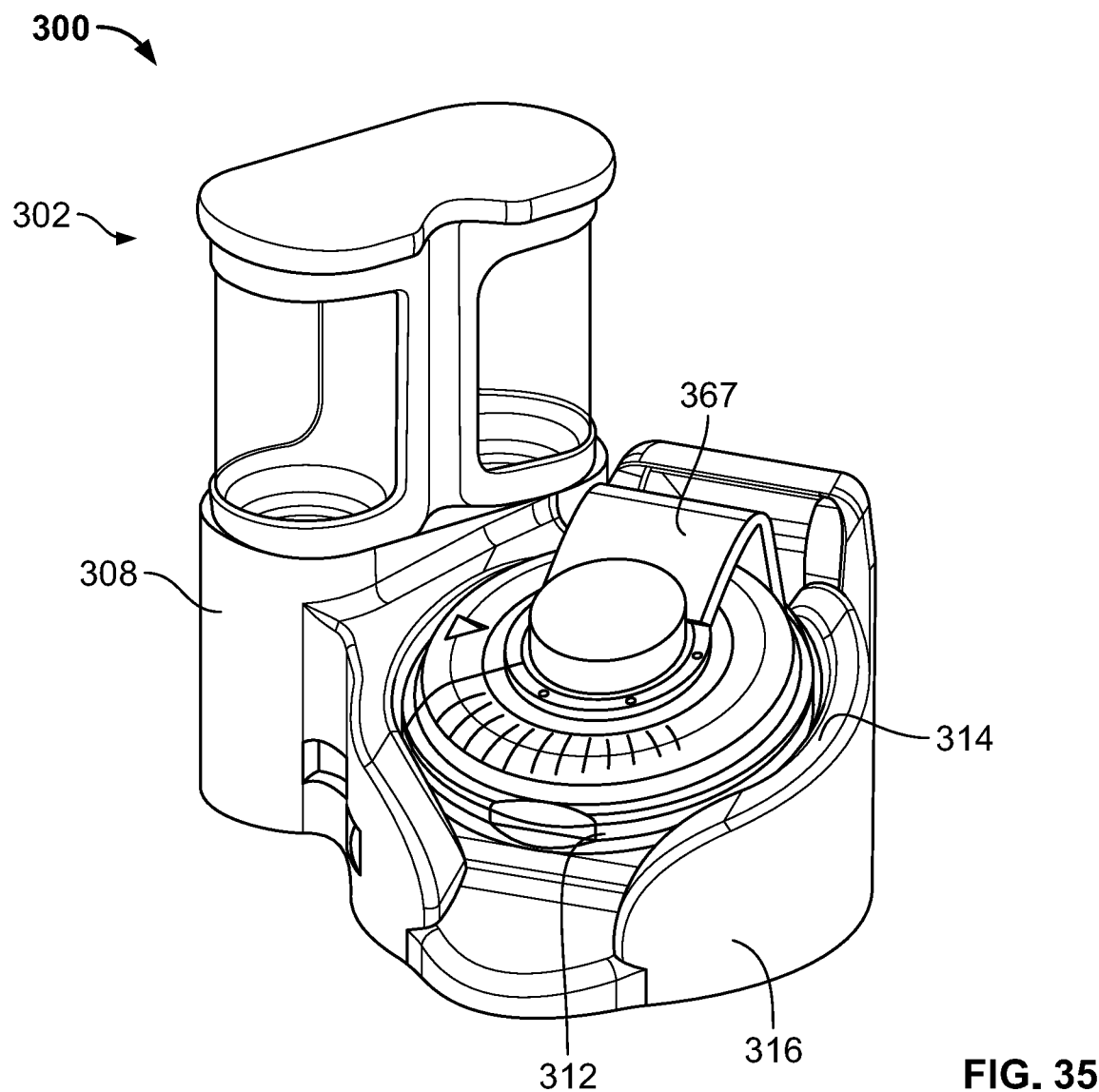
FIG. 35 is a perspective view of a transfer device for temporary coupling to an injection device for manipulating/mixing/transferring an injectable from a plurality of vials into the injection device.
Figure 36:
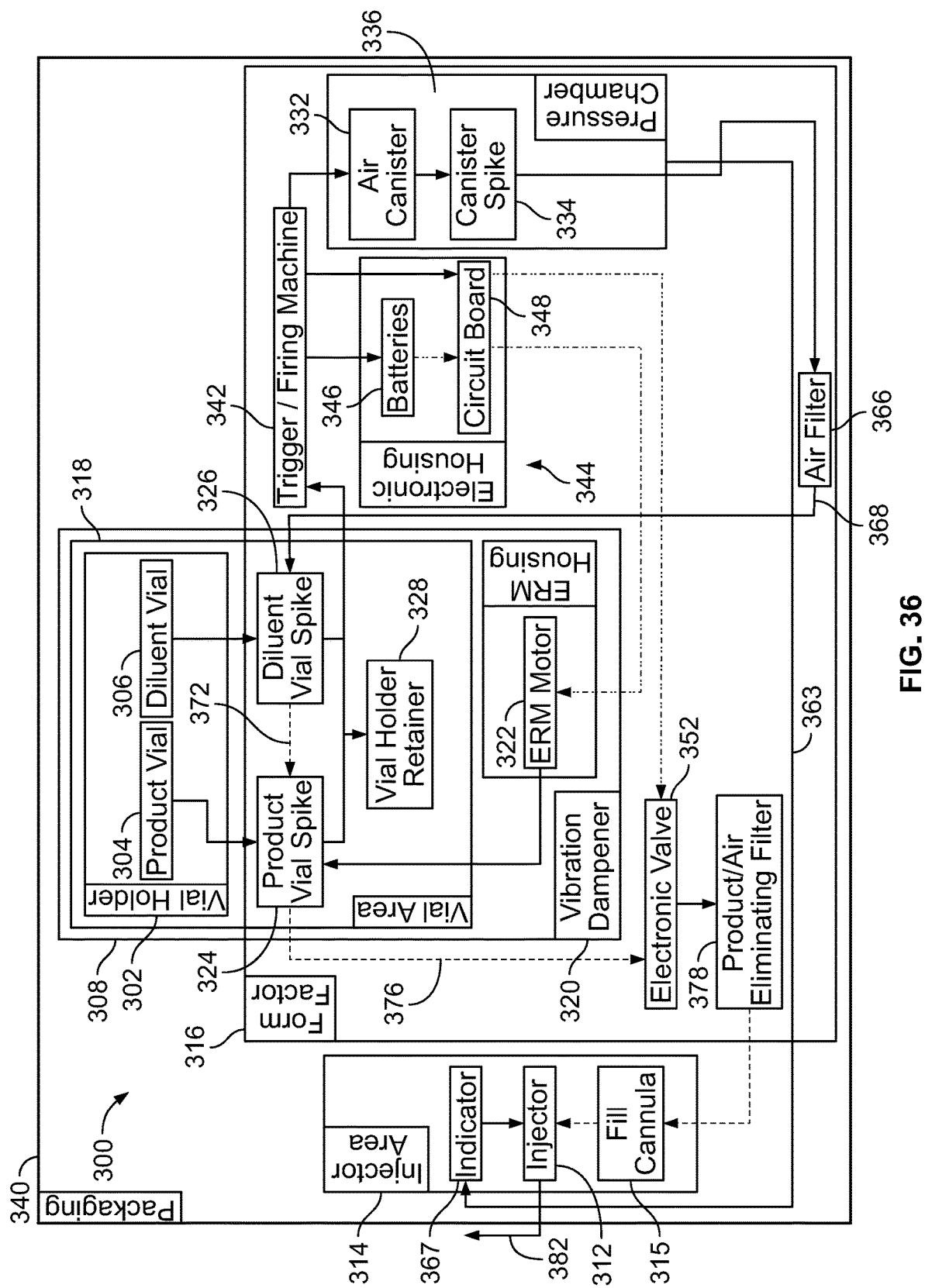
FIG. 36 is schematic of an embodiment of the transfer device of FIG. 35.

A device for automatically reconstituting a lyophilized drug and transferring the reconstituted drug to an injection device is indicated in general at 300 in FIGS. 35 and 36. In this embodiment, as explained in greater detail below, a user inserts a vial holder, indicated in general at 302 in FIG. 35, that contains inverted lyophilized drug and diluent vials (304 and 306 of FIG. 36), into a vial receptacle 308 of the device. In addition, the device removably receives an injection device 312 within a corresponding recess of an injection device receptacle 314. As in the embodiment described previously, the bottom of the recess of the injection device receptacle includes an injection device fill cannula (315 in FIG. 36, not visible in FIG. 35) that penetrates a fill port of the injection device.

As an example only, the vial holder 302 may be constructed and used as described in commonly owned prior published PCT Application No. WO 2016/154413 A1, International Filing Date Mar. 23, 2016, which is hereby incorporated by reference herein in its entirety.

When the device 300 is activated, diluent flows from the diluent vial to the lyophilized drug vial, and the lyophilized drug vial is vibrated to promote mixing and reconstitution of the drug. The reconstituted drug is then automatically transferred from the (formerly) lyophilized drug vial (now a reconstituted drug or product vial) to the injection device 312. The injection device may then be removed from the injection device receptacle 314 of the device and used to inject the drug into the user.

As an example only, the injection device described above with respect to FIGS. 1-20 may be used as the injection device 312 of FIG. 35.

As indicated in FIGS. 35 and 36, the device includes a housing 316 that serves as a base and contains the operational components of the device.

Figure 37:
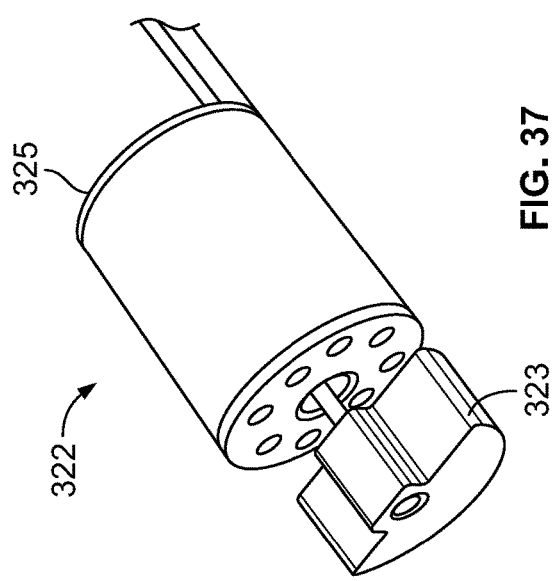
FIG. 37 is a perspective view of an eccentric reciprocating mass motor suitable for use in the transfer device of FIGS. 36 and 37.

As illustrated in FIG. 36, the vial receptacle 308 of the device includes a vial holder carriage 318 that is positioned within the housing 316. The vial holder carriage 318 includes a socket that removably receives the vial holder 302 and is operatively connected to an eccentric rotating mass (ERM) motor 322. An embodiment of the ERM motor is indicated in general at 322 in FIG. 37, wherein the eccentric rotating mass is indicated at 323 and mounted to the shaft of motor 325. As a result, when the ERM motor is activated, the vial holder carriage 318 shaken or vibrated and the vials 304 and 306 are also shaken or vibrated. ERM motor 322 is preferably electrically operated and such motors are known and available in the prior art. In addition alternative motors and vibration systems known in the art may be employed in place of the ERM motor.

In alternative embodiments of the device, the lyophilized drug vial and the diluent vial may be individually inserted into the vial receptacle 308 of the device (such as in individual sockets) with only the lyophilized drug vial shaken or vibrated by the motor.

A vibration dampener 320 is also connected between the vial holder carriage 318 and the housing and is configured so that the ERM motor vibrates the vials at the desired frequency.

As illustrated in FIG. 36, the vial holder carriage 318 also includes a product or lyophilized vial spike 324 and a diluent vial spike 326. These spikes include hollow cannulas that are automatically placed in fluid communication with the interiors of the corresponding vials when the vial holder 302 is inserted into the socket of the vial holder carriage. In alternative embodiments, the vial spikes 302 and 304 may be configured so that they are raised upon activation of the device 300 to place them in fluid communication with the vials 304 and 306.

Additional details regarding embodiments of the vial spikes 302 and 304 are provided in commonly owned prior published PCT Application No. WO 2016/154413 A1, International Filing Date Mar. 23, 2016, which was previously incorporated by reference.

The vial holder carriage 318 also includes a vial holder retainer mechanism 328 that locks the vial holder 302 into the socket of the vial holder carriage so that it cannot be removed after the device 300 is activated, and until the reconstituted drug has been transferred to the injection device.

As indicated at 332 in FIG. 36, the housing 316 contains a canister 332, which contains pressurized air. The air canister 332 is preferably a single use component, and is illustrated as such in FIG. 36, but in alternative embodiments it may be refillable. As will be explained in greater detail below, upon activation of the device 300, a canister spike 334 is configured to puncture the air canister 332 to pressurize a pressure chamber 336 and to provide air for the fluid transfer stages of operation through the spike. An embodiment of the air canister 332 and canister spike 334 is provided in commonly owned prior published PCT Application No. WO 2016/154413 A1, International Filing Date Mar. 23, 2016, which was previously incorporated by reference.

The transfer device 300, vial holder 302 (which may or may not include vials 304 and 306) and injection device 312 may be placed within packaging 340 so as to permit sale, transport and storage of the components as a single unit.

The activation of the device 300 is initiated by a trigger mechanism 342, which interacts with electronics 344 having batteries 346 and an electronic controller or circuit board 348 for energizing and controlling the ERM motor 322 and electronic valve 352 (the purpose of which will be described below). The trigger mechanism also is mechanically connected to the air canister 332 and canister spike 334 so that when the trigger mechanism is tripped, the canister spike 334 engages the air canister 332.

As examples only, the trigger mechanism 342 may include a button on the bottom of, or a lever within, the socket of the vial holder receptacle that is configured to be engaged and articulated or tripped when the when the vial holder 302 is inserted therein.

Operation of the device will now be explained with reference to FIGS. 36 and 38.

Figure 38:
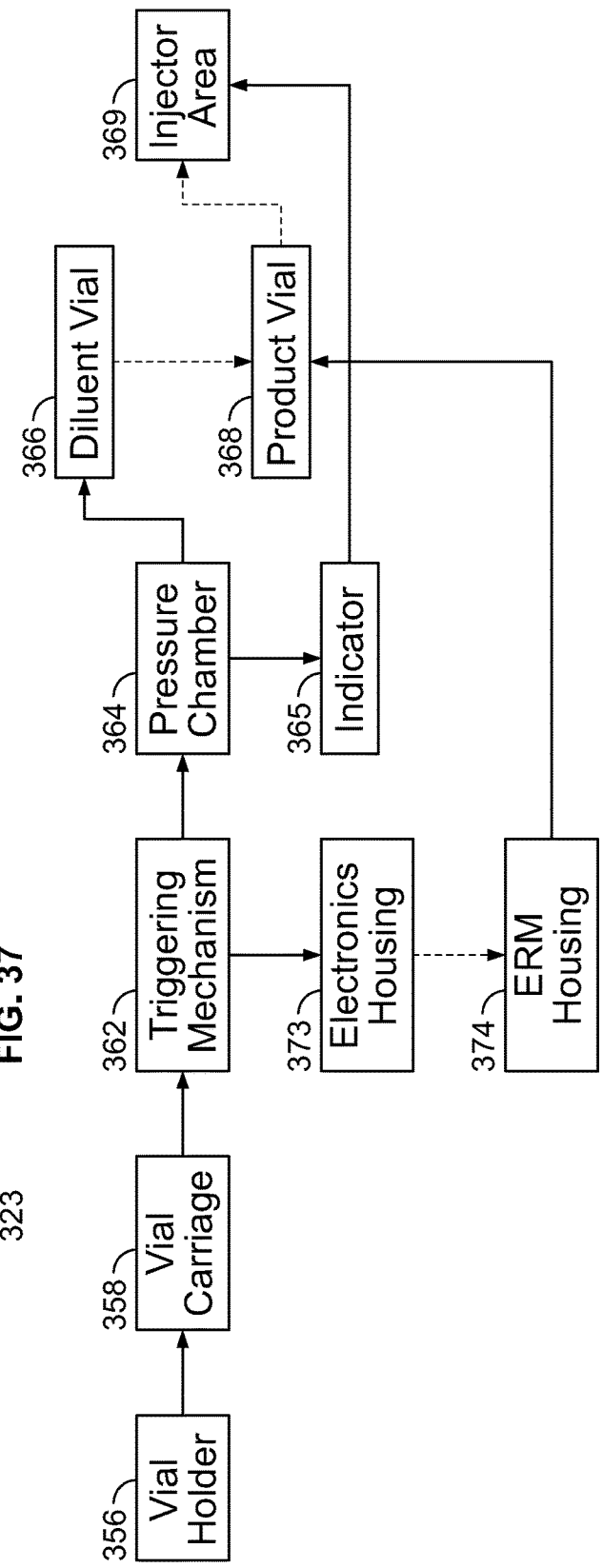
FIG. 38 is a flow diagram illustrating operation of the transfer device of FIGS. 35 and 36.

As indicated at blocks 356 and 358 in FIG. 38, the vial holder 302 (FIG. 36), which contains the inverted lyophilized drug vial 304 and diluent vial 306, is inserted into vial carriage 318. This causes the lyophilized drug/product vial spike 324 and the diluent vial spike 326 to be placed in fluid communication with the interior of the vials 304 and 306 and the vial holder retainer 328 to lock the vial holder within the device.

The insertion of the vial holder also trips the trigger mechanism 342, as indicated by block 362 of FIG. 38. When this occurs, as indicated by block 364, the air canister 332 is punctured by the canister spike 334 so that the pressure chamber 336 is pressurized.

As indicated by block 365, pressurized air from the pressurized chamber 336 flows through line 363 of FIG. 36 to an indicator 367 of the injection device receptacle 314. As illustrated in FIG. 35, the indicator 367 is essentially an arm pivotally attached to the base at its lower or proximal end with an inverted hook portion at the distal end. The initial position of the indicator 367 (such as when the transfer device is packaged with the injection device installed) is as shown in FIG. 35, and a pressure sensing mechanism allows the indicator 367 to swing out of the way of the injection device (i.e. move out of the position shown in FIG. 35) once the mixing and fluid transfer to the injection device is complete.

In the embodiment of FIG. 36 of the application, the pressure mechanism of the hook shaped piece/indicator 367 detects the pressure increase in the pressure chamber 336 via line 363, but maintains hook shaped piece 367 in the position shown in FIG. 35. When the pressure in the pressure chamber 336 decreases after the fluid has been transferred to the injector, however, the mechanism detects this pressure decrease and moves the hook shaped piece/indicator 367 out of the way so that the injector may be removed from the transfer device (as represented by block 369 of FIG. 38).

In addition, the canister spike 334, which includes a cannula, receives pressurized air from the air canister 332 which flows through air filter 366 (FIG. 36) and line 368 to the diluent vial spike 326 and diluent vial 306, as indicated by block 366 of FIG. 38. As indicated by block 368 of FIG. 38, the pressurized air entering the diluent vial 306 forces the diluent liquid from the vial 306, through line 372 (FIG. 36) to lyophilized drug/product vial 304 where it combines with the lyophilized drug therein.

It should be noted that electronic valve 352 is configured to be in the closed condition at this time so that no liquid flows out of vial 304.

A second primary function occurs within the device 300 when the trigger mechanism is activated. More specifically, with reference to block 373 of FIG. 38, the electronics 344 of FIG. 36 are activated so that the batteries 346 provide power to the ERM motor 322 under the control of circuit board 348, as indicated by block 374. The circuit board may be programmed to provide a slight delay before activation of the ERM motor 322 to provide time for the transfer of diluent to the lyophilized drug/product vial 304.

When the ERM motor 322 is energized, as described previously, it vibrates or shakes the vial holder carriage 318, and thus the vial holder 302 and vial 304 (block 368 in FIG. 38), to mix the diluent and lyophilized drug within the vial 304.

After a predetermined period of time has passed, the circuit board 348 turns off the ERM motor 322 and opens the electronic valve 352. This permits the reconstituted drug from the vial 304 to travel through line 376 (FIG. 36), electronic valve 352, filter 378 and fill cannula 315 and into the injection device 312, as indicated by blocks 368 and 369 of FIG. 38.

The pressure chamber 336, line 363 or the mechanism of indicator 367 may be provided with an orifice or other feature which permits the pressure within the chamber 336 to decay after a period of time sufficient for the functionality of FIG. 38 to be performed so that the indicator 367 retracts from the orientation illustrated in FIG. 35 (such as by a spring). This provides an indication that the injection device 312 has been filled and permits removal of the injection device 312 from the transfer device 300 (as indicated by arrow 382 of FIG. 36.

It should be understood that the pressure chamber 336 of FIG. 36, and associated air canister 332 and canister spike 334 components, could be replaced with an alternative source of pressurized air in alternative embodiments, such as an air pump or external source of pressurized air.

The basis of the technology of the automated transfer device of FIGS. 35-38 is enhanced particle and liquid dispersion in the lyophilized drug/product vial due to the vibrating liquid (agitation energy). Frequencies may be relatively low (<500 Hz), reducing the risk of cavitation or other high frequency induced protein degradation (temperature or bubble formation).

As explained above, the lyophilized drug is captured within a vial holder in an inverted position as it would be used. The vial holder is coupled to the eccentric rotating mass (ERM) motor. Varying pulse width modulation (PWM) signals and ERM weights allow for the accommodation of a range of frequencies and amplitudes that the drugs may be exposed to. Furthermore, the electronics controlling the system (such as the circuit board 348 of FIG. 36) may be adjusted or programmed to provide a desired vibration/mixing duration suitable for the lyophilized drug being reconstituted. The technology is adaptable for a range of drug products due to the flexibility in the variables inherent in the technology (amplitude and frequency).

As examples only, the frequency of the ERM motor may be 5000 rpm (83.3 Hz) to 20,000 rpm (333.3 Hz), while the amplitude may be 0.38 G to 10 G.

The automated transfer device of FIGS. 35-38 provides a number of advantages, including use of standard container closure vials, automatic mixing of contents of two vials, a mixing process that may be customized for the drug, a mixing process that is validated and repeatable, automatic loading of the injector when mixing is complete and an injector that is ready for use immediately after mixing and transfer. Furthermore, the transfer device offers simple operation in that, in order to activate the device, the user simply inserts the vial holder into the system.

ASPECTS

The present subject matter includes various aspects which may be in addition to those set forth above, such as:

Aspect 1. A disposable fluid transfer device comprising an injector support surface configured to receive an injection device thereon, a fluid transfer port extending upwardly from the support surface for transfer of liquid into an injection device when received on the support surface, a lyophilized drug vial adapter configured to receive a vial containing a lyophilized drug, a diluent vial adapter configured to receive a vial containing a diluent, a syringe adapter configured to receive a syringe, a fluid flow path that may be placed in communication between the lyophilized drug vial adapter and syringe adapter, between the diluent vial adapter and the syringe adapter and between the syringe adapter and the fluid transfer port, and a manual valve in the fluid flow path for selectively placing the diluent vial adapter in communication with the syringe adapter, placing the lyophilized drug vial adapter in communication with the syringe adapter or placing the syringe adapter in communication with fluid transfer port.

Aspect 2. The disposable fluid transfer device of aspect 1 including a releasable harness for holding an injection device coupled to the transfer device.

Aspect 3. The disposable fluid transfer device of aspect 1 including an injection device coupled thereto and releasably held in the coupled position.

Aspect 4. The disposable fluid transfer device of aspect 3 in which the injection device includes and internal resilient expandable member and a filling port for introducing liquid into the expandable member and wherein the fluid transfer port of the transfer device extends into the filling port when the injection device is coupled to the transfer device.

Aspect 5. The disposable transfer device of aspect 1 in which the support has an upper face and a lower face, the injection device being receivable against the upper face, and the valve and fluid flow path being carried on the lower face of the support surface.

Aspect 6. A device for reconstituting a lyophilized product comprising a housing including a vial receptacle; a vial holder configured to be connected to the vial receptacle of the housing and to hold a first vial containing a lyophilized product and a second vial containing a diluent; a pressurized fluid supply system configured to transfer diluent from the second vial to the first vial; a motor configured to be connected to the vial holder when the vial holder is connected to the vial receptacle and to vibrate the first vial so that the lyophilized product in the first vial is reconstituted with diluent transferred from the second vial to the first vial.

Aspect 7. The device of aspect 6 wherein the lyophilized product includes a drug.

Aspect 8. The device of any one of aspects 6 and 7 further comprising a trigger mechanism and an electronic controller, wherein the electronic controller is configured to control the motor and the trigger mechanism is connected to the vial receptacle and the electronic controller.

Aspect 9. The device of aspect 3 further comprising a vial holder carriage configured to receive the vial holder and to activate the trigger mechanism when the vial holder is connected to the vial holder carriage and wherein the motor is configured to vibrate the vial holder carriage.

Aspect 10. The device of aspect 9 further comprising a vial retainer configured to lock the vial holder within the vial holder carriage after the vial holder is inserted into the vial holder carriage.

Aspect 11. The device of any one of aspects 6-10 wherein the motor is an eccentric rotating mass motor.

Aspect 12. The device of any one of aspects 6-11 wherein the housing further comprises and an injection device receptacle, said injection device receptacle configured to receive an injection device and wherein the pressurized fluid supply system is further configured to transfer reconstituted product from the first vial to an injection device connected to the injection device receptacle.

Aspect 13. The device of any one of aspects 6-12 wherein the motor is configured to vibrate the first vial at a frequency below 500 Hz.

Aspect 14. The device of any one of aspects 6-13 further comprising a vibration dampener configured to be connected to the vial holder when the vial holder is connected to the vial receptacle of the housing.

Aspect 15. The device of any one of aspects 6-14 wherein the vial holder is configured to hold the first and second vials in inverted positions.

Aspect 16. A system for injecting a drug comprising an injection device; a device for reconstituting a lyophilized drug comprising i) a vial holder configured to hold a first vial containing a lyophilized drug and a second vial containing a diluent; ii) a pressurized fluid supply system configured to transfer diluent from the second vial to the first vial and to transfer a reconstituted drug from the first vial to the injection device; iii) a motor connected to the vial holder and configured to vibrate the first vial so that the lyophilized drug in the first vial is reconstituted with diluent transferred from the second vial to the first vial Aspect 17. A method for reconstituting a drug comprising the steps of: providing a first vial containing a lyophilized drug and a second vial containing a diluent; transferring diluent from the second vial to the first vial; vibrating the first vial so that the lyophilized drug in the first vial is reconstituted with the diluent from the second vial.

Aspect 18. The method of aspect 17 wherein the vibration occurs at a frequency below 500 Hz.

Aspect 19. A device for reconstituting a lyophilized product comprising a vial receptacle configured to hold a first vial containing a lyophilized product and a second vial containing a diluent; a pressurized fluid supply system configured to transfer diluent from the second vial to the first vial; a motor configured to vibrate the first vial when the first vial is held by the vial receptacle so that the lyophilized product in the first vial is reconstituted with diluent transferred from the second vial to the first vial.

Aspect 20. The device of aspect 19 further comprising an injection device receptacle, said injection device receptacle configured to receive an injection device and wherein the pressurized fluid supply system is further configured to transfer reconstituted product from the first vial to an injection device connected to the injection device receptacle.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A disposable fluid transfer device comprising a base including an injector support surface configured to receive an injection device thereon, a fluid transfer port extending upwardly from the support surface for transfer of liquid into an injection device when received on the support surface, a lyophilized drug vial adapter configured to receive a vial containing a lyophilized drug, a diluent vial adapter configured to receive a vial containing a diluent, said lyophilized drug vial adapter and said diluent vial adapter positioned on a first side of the base and configured so that insertion of vials into the lyophilized drug vial adaptor and the diluent vial adapter is in a direction whereby the vials move parallel to each other and the injector support surface, a syringe adapter configured to receive a syringe, said syringe adapter positioned on a second side of the base that is opposite the first side of the base, a fluid flow path that may be placed in communication between the lyophilized drug vial adapter and syringe adapter, between the diluent vial adapter and the syringe adapter and between the syringe adapter and the fluid transfer port, and a manual valve in the fluid flow path for selectively placing the diluent vial adapter in communication with the syringe adapter, placing the lyophilized drug vial adapter in communication with the syringe adapter or placing the syringe adapter in communication with fluid transfer port, said support surface having an upper face and a lower face with the injection device being receivable against the upper face and the valve and fluid flow path being carried on the lower face of the support surface, and said manual valve including a flow control member for configuring the valve, said flow control member extending from a third side of the base that separates the first and second sides of the base.

2. The disposable fluid transfer device of claim 1 including a releasable harness for holding an injection device coupled to the transfer device.

3. The disposable fluid transfer device of claim 1 including an injection device coupled thereto and releasably held in the coupled position.

4. The disposable fluid transfer device of claim 3 in which the injection device includes and internal resilient expandable member and a filling port for introducing liquid into the expandable member and wherein the fluid transfer port of the transfer device extends into the filling port when the injection device is coupled to the transfer device.

* * * * *